(12) United States Patent
Bessodes et al.

(10) Patent No.: US 7,641,914 B2
(45) Date of Patent: Jan. 5, 2010

(54) ACID-SENSITIVE COMPOUNDS, THEIR PREPARATION AND USES

(75) Inventors: Michel Bessodes, Villejuif (FR); Christophe Masson, Montgeron (FR); Daniel Scherman, Paris (FR); Barbara Wetzer, Paris (FR)

(73) Assignee: Gencell, S.A. (FR)

( * ) Notice: Subject to any disclaimer, the term of this patent is extended or adjusted under 35 U.S.C. 154(b) by 695 days.

(21) Appl. No.: 11/054,612

(22) Filed: Feb. 10, 2005

(65) Prior Publication Data

US 2005/0222434 A1 Oct. 6, 2005

Related U.S. Application Data

(63) Continuation of application No. 09/972,854, filed on Oct. 10, 2001, now abandoned.

(60) Provisional application No. 60/239,116, filed on Oct. 11, 2000.

(51) Int. Cl.
*A61K 9/127* (2006.01)
*A61K 31/70* (2006.01)
*A01N 43/04* (2006.01)

(52) U.S. Cl. .................... 424/450; 514/23; 514/44; 514/54

(58) Field of Classification Search .................. None
See application file for complete search history.

(56) References Cited

U.S. PATENT DOCUMENTS

| | | | |
|---|---|---|---|
| 4,406,686 A | 9/1983 | Walker et al. | |
| 5,965,434 A | 10/1999 | Wolff et al. | |
| 6,013,240 A | 1/2000 | Behr et al. | |
| 6,200,599 B1 * | 3/2001 | Nantz et al. | 424/450 |
| 6,849,272 B1 * | 2/2005 | Langer et al. | 424/489 |

FOREIGN PATENT DOCUMENTS

| | | |
|---|---|---|
| WO | WO 96/02655 A1 | 2/1996 |
| WO | WO 96/17823 A1 | 6/1996 |
| WO | WO 97/18185 A1 | 5/1997 |
| WO | WO 97/31624 A1 | 9/1997 |
| WO | WO 98/34648 A1 | 8/1998 |
| WO | WO 98/54130 A1 | 12/1998 |
| WO | WO 99/51581 A1 | 10/1999 |
| WO | WO 00/75164 A1 | 12/2000 |

OTHER PUBLICATIONS

Guo, X. et al., "Steric Stabilization of Fusogenic Liposomes by a Low-pH Sensitive PEG—Diortho Ester-Lipd Conjugate," Bioconjugate Chem., 12:291-300 (2001).
Kratz, F. et al., "Drug Polymer Conjugates Containing Acid-Cleavable Bonds," Crit. Rev. Therap. Drug Carrier Syst., 16:245-288 (1999).
Papahadjopoulos, D. et al., "Sterically Stabilized Liposomes: Improvements in Pharmacokinetics and Antitumor Therapeutic Efficacy," Proc. Natl. Acad. Sci. USA., 88:11460-11464 (1991).
Raghunand, N., et al., "pH and Drug Resistance in Tumors," Drug Resistance Updates 3:39-47 (2000).
Rodrigues et al., "Acid Sensitive Polyethylene Glycol Conjugates of Doxorubicin: Preparation, In Vitro Efficacy and Intracellular Distribution," Bioorganic and Medicinal Chemistry, 7:2517-2524 (1999).
Rui, Y., et al., "Displasmenylcholine-Folate Liposomes: An Efficient Vehicle for Intracellular Drug Delivery," Jour. American Chemical Society, 120:11213-11218 (1998).
Torchilin, V.P., et al., "Poly(ethylene glycol) on the Liposome Surface: On the Mechanism of Polymer-coated Liposome Longevity," Biochimica et Biophysica Acta, 1195:11-20 (1994).
Volk, T., et al., "pH in Human Tumor Xenografts: Effect of Intravenous Administration of Glucose," Br. J. Cancer, 68:492-500 (1993).
Yatvin, M.B., et al., "pH-Sensitive Liposomes: Possible Clinical Implications," Science, 210:1253-1255 (1980).
Zhu, J., et al., "Self-Cleaning Ortho Ester Lipids: A New Class of pH-Vulnerable Amphiphiles," J. Am. Chem. Soc., 122:2645-2646 (2000).

* cited by examiner

*Primary Examiner*—Traviss C McIntosh, III
(74) *Attorney, Agent, or Firm*—Finnegan, Henderson, Farabow, Garrett & Dunner, LLP

(57) ABSTRACT

Novel acid-sensitive compounds comprising a cyclic orthoester that is acid-sensitive, and their salts, and comprising at least one hydrophilic substituent. These compounds are useful, for example, for forming conjugates (liposomes, complexes, nanoparticles and the like) with biologically active substances and releasing them into cellular tissues or compartments whose pH is acidic, or as nonionic surfactant for stabilizing particles encapsulating a biologically active substance and then destabilizing them in acid medium, or alternatively as a vector covalently linked to a therapeutic molecule so as to release said therapeutic molecule into the cellular tissues or compartments whose pH is acidic.

13 Claims, 8 Drawing Sheets

Figure 1:
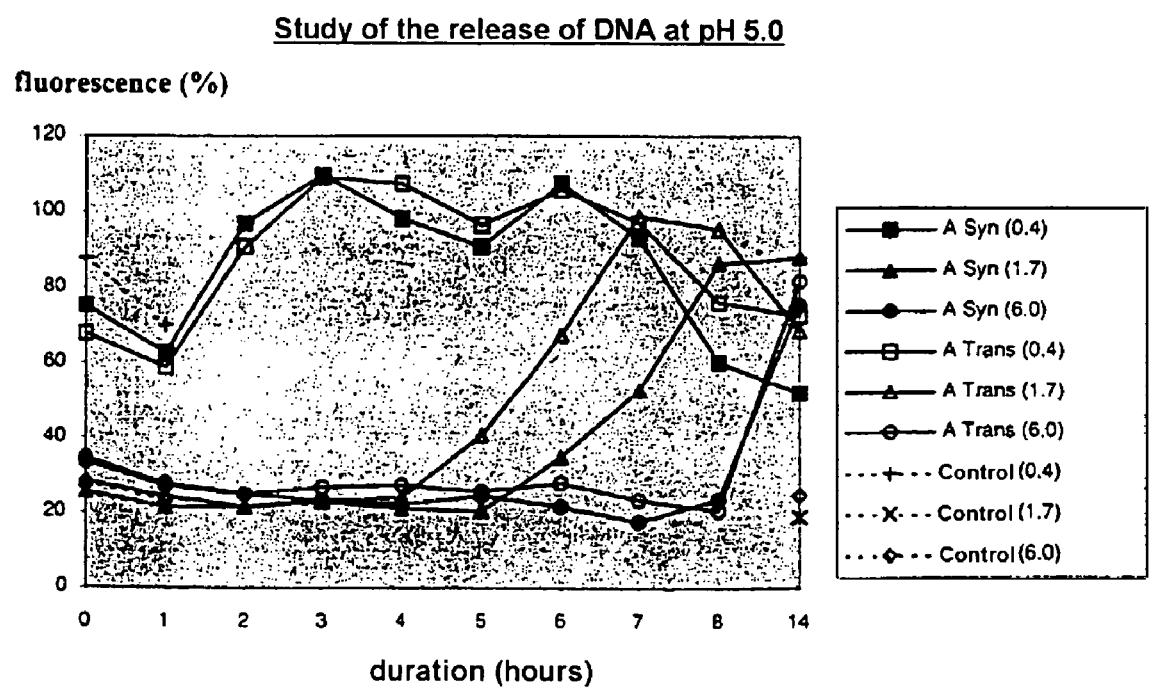

Study of the release of DNA at pH 5.0

**Efficiency of transfection *in vitro***

Stabilization of the nucleolipid complexes by compound C, compound D, BRIJ700 or analog D Weight/weight ratio with the DNA

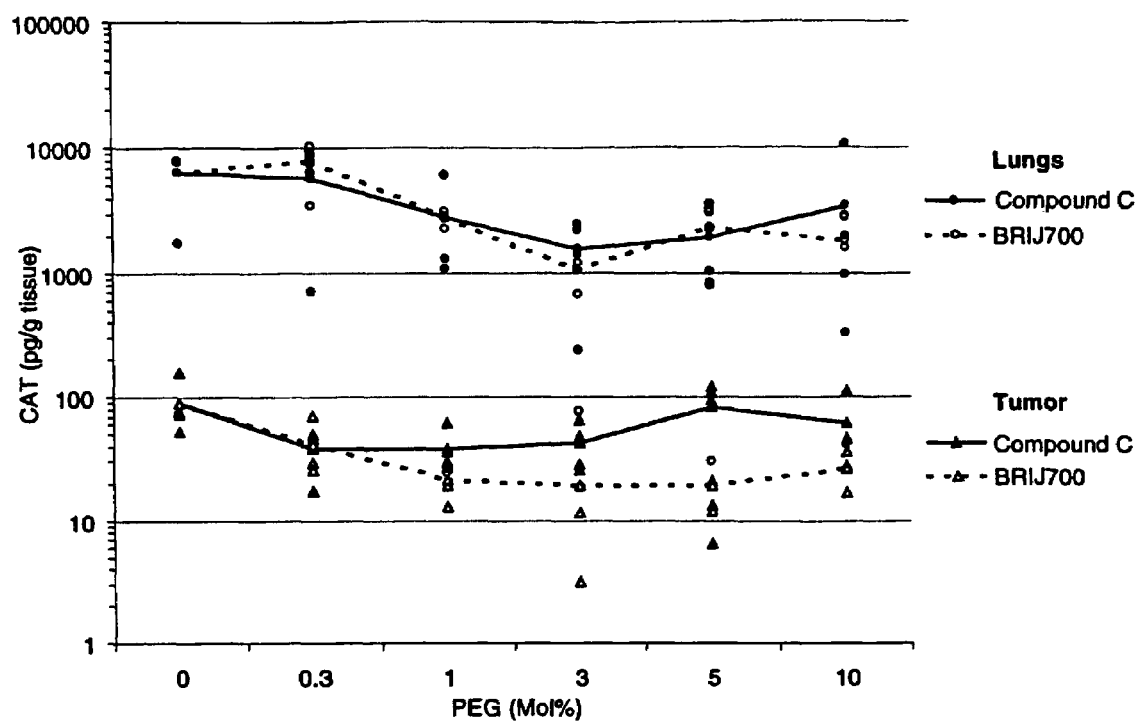
Figure 7: Dose response of pH labile $C18\text{-}PEG_{5000}$ (Compound C) on gene transfer activity in vivo mediated by a cationic lipid/DOPE/DNA (5/5/1) complex. Non-degradable $C18\text{-}PEG_{5000}$ (BRIJ700) was used as a negative control. Data are mean (lines) and individual values of 4 Balb/C mice bearing subcutaneous M109 tumor.

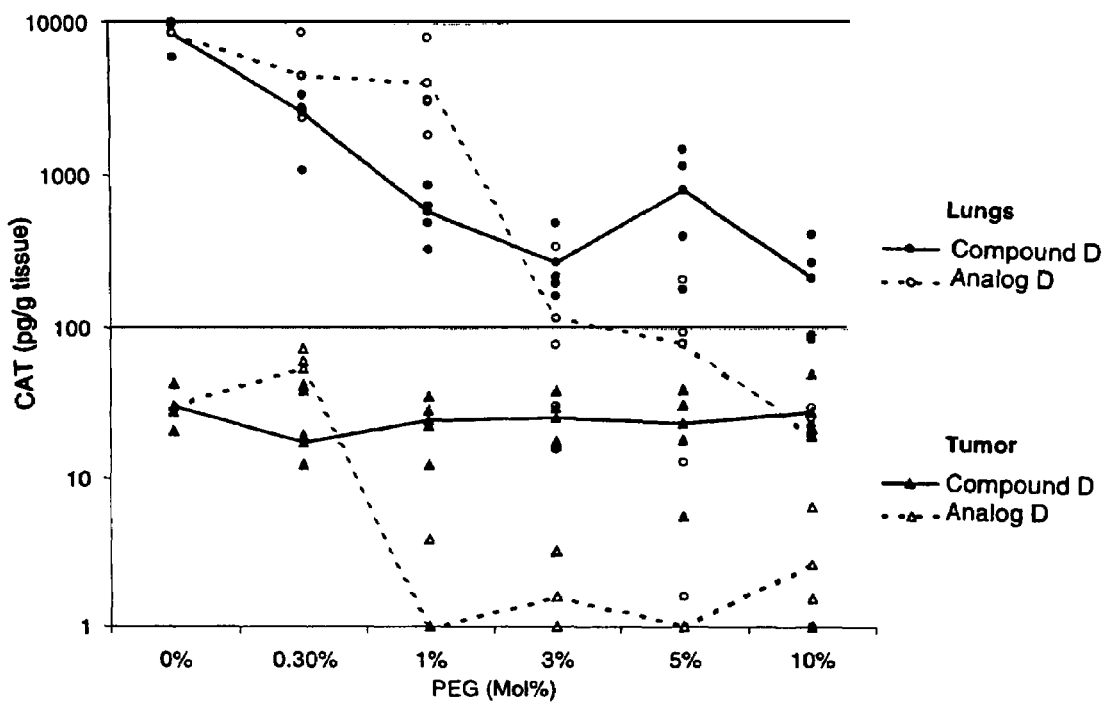
Figure 8: Dose response of pH labile cholesterol-$PEG_{5000}$ (Compound D) on gene transfer activity in vivo mediated by a cationic lipid/DOPE/DNA (5/5/1) complex. Non-degradable cholesterol-$PEG_{5000}$ (Analog D) was used as a negative control. Data are mean (lines) and individual values of 4 Balb/C mice bearing subcutaneous M109 tumor.

ACID-SENSITIVE COMPOUNDS, THEIR PREPARATION AND USES

CROSS REFERENCE TO RELATED APPLICATIONS

This is a continuation of application Ser. No. 09/972,854, filed Oct. 10, 2001, now abandoned, which claims the benefit of U.S. Provisional Application No. 60/239,116, filed Oct. 11, 2000, both of which are incorporated herein by reference.

The present invention relates to acid-sensitive compounds and their preparation. These compounds comprise at least one hydrophilic substituent and a cyclic ortho-ester, which is acid-sensitive. These compounds are generally useful, for example, for forming conjugates (liposomes, complexes, nanoparticles and the like) with biologically active substances and releasing them into cellular tissues or compartments whose pH is acidic, or as nonionic surfactant for stabilizing particles encapsulating a biologically active substance and then destabilizing them in acid medium, or alternatively as a vector covalently linked to a therapeutic molecule so as to release it into the cellular tissues or compartments whose pH is acidic.

The release of biologically active substances into tissues or cells having an increased acidity relative to what is physiologically normal is a known problem that has been the subject of numerous studies, without giving completely satisfactory results up until now. Thus, many pH-sensitive liposomes have been designed so as to release biologically active substances by taking advantage of the acidification of certain tissues or of the endosome.

For example, Yatvin et al. (*Science*, Vol. 210, 1980, pp. 1253-4) designed pH-sensitive lipids capable of becoming inserted into the lipid bilayer of conventional liposomes, of formula:

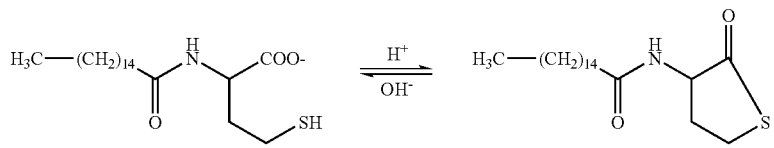

The homocysteine present in this lipid is in its open form at neutral or alkaline pH and resembles, in this case, a fatty acid which becomes perfectly inserted into the bilayer of the liposomes. At this pH, it exists in its closed form: it then forms a cyclic thiolactone, thus resembling a neutral lipid that destabilizes the liposomal bilayer and thus promotes the release of the active substance. Such a molecule promotes the release of medicinal molecules in the regions of the body wherein the pH is less than the physiological pH, for example in primary tumors, metastases, or alternatively sites of inflammation and of infection.

U.S. Pat. No. 5,965,434 proposes amphiphatic lipids comprising a cationic pH-sensitive hydrophilic part of formula:

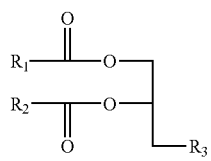

wherein $R_1$ and $R_2$ represent, independently of each other, $CH_3(CH_2)_{14}$, $CH_3(CH_2)_{12}$, $CH_3(CH_2)_7CHCH(CH_2)_7$, and $R_3$ represents a substituent 1-methylimidazole, imidazole, 4,9-dioxo-1,12-dodecanediamine, cysteamine, 1-(3-aminopropyl)imidazole, morpholine, 4-aminopyridine, pyridine, guanidine, hydrazine, thiouronium or piperazine.

These compounds have the characteristic feature of carrying an overall positive charge (at the level of the compound $R_3$) which increases when the pH decreases from 8.0 to 4.5. This modification of the charge induces a conformational transformation of the liposome, allowing it to release its content. These lipids thus allow the release of medicinal molecules or of nucleic acids into acidic media whose pH varies up to 4.5.

Moreover, application WO 97/31624 proposes pH-sensitive phospholipids ("triggerable lipids") which comprise a vinyl ether function which may be degraded in the cytoplasm, and which have the general formula:

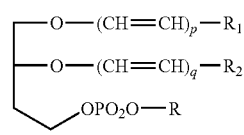

wherein p and q are equal to 0 or 1, at least one of the two being equal to 1, $R_1$ and $R_2$ represent, independently of each other, an alkyl or an alkene containing 12 to 24 carbon atoms, and R represents a group chosen from 2-aminoethyl, 2-(trimethylamino)-ethyl, 2-(N,N-dimethylamino)ethyl, 2-(trimethyl-ammonium)ethyl, 2-carboxy-2-aminoethyl, succinamido-ethyl or inosityl.

These phospholipids are mixed with other phospholipids, which are themselves complexed with cell receptor ligands, so as to form liposomes capable of undergoing conformational changes at acidic pH. Such liposomes allow the encapsulation of numerous medicinal substances and also of nucleic acids for gene therapy.

Another approach has also been described (Kratz et al., Crit. Rev. Ther. Drug Carrier Syst. 1999, 16(3), pp. 245-88) wherein a therapeutic molecule is covalently linked to a polymer via an acid-sensitive bond so as to ensure the release of said therapeutic molecule into weakly acidic tumor tissues or alternatively into the endosomes and lysosomes after cellular internalization of the polymeric conjugate. Numerous possible bonds have thus been described, for example acetal, disulfide, hydrazone, cis-aconitrile, trityl or alternatively silylated ether bonds.

However, all the pH-sensitive compounds developed up until now have the disadvantage of not being modulable as regards their sensitivity. Thus, it would be highly advantageous to be able to have acid-labile compounds whose sensitivity could be modulated according to, for example, the tissues or cells targeted, the biologically active substance to be released or, alternatively, the applications envisaged.

To solve this problem, the Applicants have thus developed a novel family of acid-sensitive compounds, or salts thereof, comprising a cyclic ortho-ester and at least one hydrophilic substituent chosen from polyalkylene glycols, monosaccharides, polysaccharides, hydrophilic therapeutic molecules, or linear or branched alkyls, wherein each linear or branched alkyl comprises at least 3 carbon atoms, wherein at least one of the methylene groups is optionally replaced with an amino group that is optionally substituted, and wherein at least one terminal methyl group of said linear or branched alkyl is substituted with at least one primary amine, secondary amine, tertiary amine, quaternary amine, guanidine or cyclic guanidine.

Such compounds are useful for the vectorization and the release of biologically active substances into the acidic regions of the body by virtue of the cyclic ortho-ester function, which is acid-sensitive. They are generally advantageous because the pH-sensitivity of the compound may be modulated according to the choice of the substituent present on the central carbon and the size of the ortho-ester ring. It is thus possible to broadly vary the kinetics of hydrolysis of these compounds and, therefore, to modulate the time necessary for the release of the biologically active substance. In addition, the acid-sensitive compounds according to the present invention can be advantageously degraded in acidic medium in an autocatalytic manner. Indeed, the partial degradation of the acid-sensitive compounds according to the invention causes the gradual release of an acid (for example, formic acid when the starting compound is derived from an ortho-formate, or alternatively acetic acid when the starting compound is derived from an ortho-acetate, or alternatively benzoic acid when the starting compound is derived from an ortho-benzoate) that induces a decrease in the pH, further promoting their degradation.

In one embodiment of the present invention, the acid-sensitive compounds according to the present invention have the general formula:

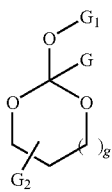

wherein:

g is an integer chosen from 0, 1, 2, 3 or 4,

G is a group chosen according to the pH-sensitivity that it is desired to confer on the compound, $G_1$ and $G_2$ is a pair of substituents chosen from one of the following substituent pairs:

(a) wherein one substituent is a hydrophilic substituent chosen from a linear or branched alkyl group comprising at least 3 carbon atoms, wherein at least one of the methylene groups is optionally replaced with an amino group that is optionally substituted (with a methyl group for example), and wherein at least one terminal methyl group of said linear or branched alkyl groups are substituted with at least one primary amine, secondary amine, tertiary amine, quaternary amine, guanidine, or cyclic guanidine, and the other substituent is a hydrophobic substituent chosen from single-chain alkyls, double-chain alkyls, steroid derivatives, or hydrophobic dendrimers;

(b) or wherein one substituent is a hydrophobic linear alkyl group comprising 10 to 24 carbon atoms and optionally comprising at least one unsaturation, and the other substituent is a group of formula (II):

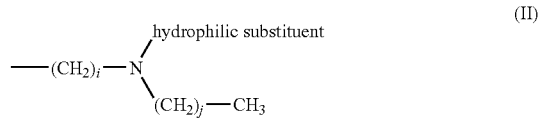

wherein i is an integer ranging from 1 to 4, j is an integer ranging from 9 to 23, and said hydrophilic substituent of formula (II) is a linear or branched alkyl comprising at least 3 carbon atoms, wherein at least one of the methylene groups is optionally replaced with an amino group that is optionally substituted (with a methyl group for example), and wherein at least one terminal methyl group of said linear or branched alkyl is substituted with at least one primary amine, secondary amine, tertiary amine, quaternary amine, guanidine, or cyclic guanidine;

(c) or wherein one substituent is a hydrophilic polyalkylene glycol, a monosaccharide, or a polysaccharide, and the other substituent is a polyalkylene imine;

(d) or wherein one substituent is a polyalkylene glycol, monosaccharide, or polysaccharide, and the other substituent is a single-chain alkyl, double-chain alkyl, steroid derivative, hydrophobic dendrimer, or a covalent conjugate between a single-chain alkyl, a double-chain alkyl, a steroid derivative, or a hydrophobic dendrimer and a polyalkylene glycol molecule comprising 1 to 20 monomeric units;

(e) or wherein one substituent is a polyalkylene glycol, a monosaccharide, or a polysaccharide, and the other substituent is a therapeutic molecule;

(f) or wherein one substituent is a hydrophilic therapeutic molecule, and the other substituent is a single-chain alkyl, a double-chain alkyl, a steroid derivative, or a hydrophobic dendrimers.

The substituent G placed on the central carbon of the ortho-ester is chosen so as to modulate the sensitivity of the acid-sensitive compound according to the present invention. Thus, the more electron-donating the group G, the more acid-sensitive the compound, and the more electron-attracting the group G, the less acid-sensitive the compound. According to one embodiment of the invention, G is chosen from a hydrogen atom, alkyl substituents comprising 1 to 6 carbon atoms in the form of a saturated or unsaturated, straight or branched chain, or aryls. In another embodiment, G is chosen from hydrogen, methyl, ethyl or phenyl. For the purposes of the present invention an "aryl group" comprises a univalent aromatic hydrocarbon group. For example, an aryl group may generally comprise 6 to 14 carbon atoms. In one embodiment of the present invention, at least one aryl group is chosen from phenyl, naphthyl groups, for example, 1-naphthyl or 2-naphthyl, biphenylyl groups, for example, 2-biphenylyl, 3-biphenylyl or 4-biphenylyl, anthryl groups, and fluorenyl groups. In another embodiment, at least one aryl group is chosen from phenyl. In yet another embodiment, at least one aryl group is chosen from phenyl, wherein said phenyl is optionally mono-substituted, disubstituted, trisubstituted, or tetrasubstituted, wherein the substituents may be the same or different from one another. For example, the substituent may be chosen from halogens, $(C_1-C_8)$alkyl groups, or $(C_1-C_8)$alkoxy groups.

Phenyl groups can be monosubstituted, such as, for example, at position-2, at position-3 or at position-4. Phenyl groups can be disubstituted, such as, for example, at positions-2,3, at positions-2,4, at positions-2,5, at positions-2,6, at positions-3,4, or at positions-3,5. Phenyl groups can be trisubstituted, such as, for example, at positions 2,3,4, at positions-2,3,5, at positions-2,4,5, at positions-2,4,6, at positions-2,3,6, or at positions-3,4,5.

According to yet another embodiment of the invention, the linear or branched alkyls comprise at least 3 carbon atoms wherein at least one of the methylene groups is optionally replaced with an amino group that is optionally substituted (with a methyl group for example) and at least one terminal methyl group is substituted with at least one primary amine, secondary amine, tertiary amine, quaternary amine, guanidine or cyclic guanidine, and include, for example, groups of the polyamine type that are already known and described in the literature for the vectorization of nucleic acids, for example in the publications WO 96/17823, WO 97/18185, WO 98/54130, and WO 99/51581. For example, this may include polyamines of formula:

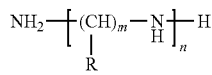

wherein
R is a hydrogen atom with the exception that one of the groups R is the covalent bond with the cyclic ortho-ester
n is an integer ranging from 1 and 9 inclusive
m is an integer ranging from 2 and 6 inclusive, it being possible for the values of m to be identical or different within the different groups —$(CH)_m$—NH—.

According to another embodiment, this may also include a group of the polyamine type of formula:

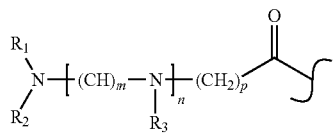

wherein:
$R_1$, $R_2$, and $R_3$ are, independently of each other, a hydrogen atom or a group —$(CH_2)_q$—NRR', wherein q is an integer chosen from 1, 2, 3, 4, 5 and 6, this being in an independent manner between the different groups $R_1$, $R_2$ and $R_3$, wherein R and R' are, independently of each other, a hydrogen atom or a group —$(CH_2)_{q'}$—$NH_2$,
wherein q' is an integer chosen from 1, 2, 3, 4, 5 and 6, this being in an independent manner between the different groups R and R',
m and p are, independently of each other, integers each ranging from 1 to 6, and
n is an integer ranging from 0 to 6, wherein when n is greater than 1, then m can be different values and $R_3$ different meanings in the formula, and wherein, when n is equal to 0, then at least one of $R_1$ and $R_2$ is different from hydrogen.

According to another embodiment of the present invention, the group of the lipopolyamine type may also be represented by a substituent with a formula identical to the preceding one, but wherein R and R' are, independently of each other, a hydrogen atom or a group of formula (1):

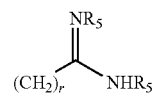

wherein r is an integer ranging from 0 to 6, and the groups $R_5$ are, independently of each other, a hydrogen atom, an alkyl, carbamate, an aliphatic acyl substituent, or an aromatic acyl substituent, that is optionally halogenated, wherein at least one of the groups $R_1$, $R_2$ and $R_3$ comprises at least one group of formula (1) in this embodiment.

A substituent of the polyamine type is thus obtained that comprises at least one terminal guanidine functions.

According to another embodiment of the invention, the group of the polyamine type may also represent a polyamine such as those described above but with a terminal group of the cyclic guanidine type (instead of an amine or a guanidine) of general formula (2):

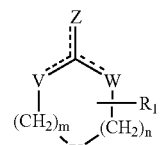

wherein:
m and n are integers, independent of each other, ranging from 0 to 3 and wherein the sum of m+n is greater than or equal to 1,
$R_1$ is a group of formula (3):

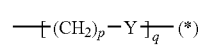

wherein p and q are integers, independent of each other, ranging from 0 to 10, Y is a carbonyl, amino, methylamino or methylene group, wherein Y is optionally different in the different groups [$(CH_2)_p$—Y], and (*) is a hydrogen atom or a covalent bond, wherein $R_1$ may be linked to any atom of formula (2), including Z, and wherein there is a single group $R_1$ in the formula (2);
X is a group $NR_2$ or a group $CHR_2$, wherein $R_2$ is a hydrogen atom or the bond with the group $R_1$ as defined above;
the group

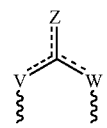

is chosen from formula 4 or formula 5,
wherein said groups of formula 4 or formula 5 are defined as follows:

*1st case: a group of general formula (4):

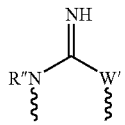
(4)

wherein W' is CHR''' or NR''', and R'' and R''' are, independently of each other, a hydrogen atom, a methyl, or the bond with the group $R_1$ as defined above, or *2nd case: a group of formula (5):

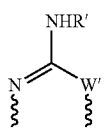
(5)

wherein W' is CHR''' or NR''', wherein R' and R''' are, independently of each other, a hydrogen atom, a methyl, or the bond with the group $R_1$ as defined above.

In general, any other substituent of the polyamine type known to persons skilled in the art for combining with nucleic acids, such as, for example, via electrostatic interactions, may also be suitable.

According to the present invention, single- or double-chain alkyls are hydrophobic constituents comprising one or two linear alkyl chains comprising 10 to 24 carbon atoms and optionally comprising at least one unsaturation. In the case of the double-chain alkyls, this may include, for example, the dialkylamino substituents wherein the alkyl substituents are linear and comprise 10 to 24 carbon atoms and optionally comprise at least one unsaturation, or alternatively this may also include saturated or unsaturated fatty acids such as, for example, palmitic acid, oleic acid, stearic acid, or myristic acid. In one embodiment of the present invention, the single- or double-chain alkyls comprise alkyl chains of 12 to 18 carbon atoms, and in another embodiment, the alkyl chains are chosen from chains of 12, 14, 16 or 18 carbon atoms.

For the purposes of the present invention a "steroid derivative" comprises substituents including, for example, sterols, steroids and steroid hormones. Also, for example, the steroid derivatives may be chosen from cholesterol, cholestanol, 3-α-5-cyclo-5-α-cholestan-6-β-ol, cholic acid, cholesteryl formate, cholestanyl formate, 3α,5-cyclo-5α-cholestan-6β-yl formate, cholesterylamine, 6-(1,5-dimethylhexyl)-3a,5a-dimethylhexadecahydrocyclopenta[a]cyclopropa[2,3]cyclopenta[1,2-f]naphthalen-10-ylamine, cholestanylamine or alternatively dexamethasone.

The hydrophobic dendrimers according to the present invention comprise, for example, hydrophobic poly(alkyl ethers) or alternatively hydrophobic poly(aryl ethers). In one embodiment of the present invention, the hydrophobic dendrimers are chosen from poly(benzyl ethers).

In another embodiment of the present invention, the polyalkylene glycols are chosen from polyalkylene glycols having an average molecular weight ranging from $10^2$ to $10^5$ Daltons (Da), and are optionally covalently linked to a targeting element. In yet another embodiment, the polyalkylene glycols according to the present invention may be chosen from polyethylene glycols (PEG) having an average molecular weight ranging from $10^2$ to $10^5$ Da, and, for example, ranging from 500 to $10^5$ Da.

For the purposes of the present invention, "mono- or polysaccharide" molecules comprise at least one saccharide, optionally covalently linked to a targeting element. For example, mono- or polysaccharides may include pyranoses and furanoses, for example glucose, mannose, rhamnose, galactose, fructose, maltose, lactose, saccharose, sucrose, fucose, cellobiose, allose, laminarobiose, gentiobiose, sophorose, melibiose and the like. Furthermore, this may also include so-called "complex" saccharides, meaning several saccharides that are covalently coupled to each other, wherein, for example, each sugar may be chosen from the list cited above. Suitable polysaccharides may include, for example, dextrans, α-amylose, amylopectin, fructans, mannans, xylans and arabinans. In one embodiment of the present invention, the mono- or polysaccharides according to the present invention are chosen from natural or commercial derivatives that are compatible with pharmacological applications such as natural sugars, cyclodextrins or alternatively dextrans.

When the polyalkylene glycol or the mono- or polysaccharide is covalently linked to a targeting element, this may include either an extracellular targeting element that makes it possible to orient the acid-sensitive compounds according to the present invention or the compositions containing them toward certain cell types or certain desired tissues (tumor cells, hepatic cells, hematopoietic cells and the like), or alternatively this may include an intracellular targeting element that promotes orientation toward certain targeted cellular compartments (mitochondria, nucleus and the like).

Among the targeting elements that can be used in the context of the invention, there may be mentioned, for example, sugars, peptides, proteins, oligonucleotides, lipids, neuromediators, hormones, vitamins or derivatives thereof. In some embodiments of the present invention, this includes sugars, peptides, vitamins or proteins, such as, for example, antibodies or antibody fragments, ligands for cellular receptors or fragments thereof, receptors or alternatively receptor fragments. For example, this may include ligands for growth factor receptors, cytokine receptors, receptors of the cellular lectin type, folate receptors, or ligands having the sequence RGD with affinity for the receptors for adhesion proteins such as integrins. There may also be mentioned the receptors for transferrin, HDLs and LDLs, or the folate transporter. The targeting element may also be a sugar that makes it possible to target lectins such as the receptors for the asialoglycoproteins or for the sialydes such as Sialyl Lewis X, or alternatively an antibody Fab fragment, or a single-chain antibody (ScFv).

According to the present invention, "polyalkyleneimines" are polymers described in the publication WO 96/02655, wherein the polymers comprise the monomeric units of general formula:

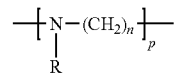

wherein R may be a hydrogen atom or a group of formula:

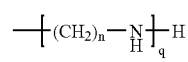

and n is an integer ranging from 2 to 10, and p and q are integers chosen such that the sum of p+q is such that the average molecular weight of the polymer ranges from 100 to $10^7$ Da.

In this formula, the value of n may vary between the different units $-NR-(CH_2)_n-$. Thus, this formula groups together both the homopolymers and the heteropolymers. Commercial polyalkyleneimines constitute an advantageous alternative. The polyethyleneimines (PEI) are one embodiment, as are PEI 25K (PEI having an average molecular weight of 25 KDa), PEI 50K, PEI 100K or alternatively PEI 200K.

Depending on the cases, each of the substituents $G_1$ and $G_2$ is either directly linked to the cyclic ortho-ester, or indirectly via a "spacer" molecule chosen from those known to persons skilled in the art. Such a "spacer" molecule makes it possible both to ensure the binding and to position the substituent(s) in question away from the cyclic ortho-ester in order to reduce any undesirable interaction between the acid-sensitive cyclic ortho-ester and its substituent(s). Examples of spacer molecules may be chosen, for example, according to the nature of the substituent $G_1$ or $G_2$ from alkyl (1 to 6 carbon atoms), carbonyl, ester, ether, amide, carbamate or thiocarbamate bonds, glycerol, urea, thiourea or a combination of several of these groups. For example, when the hydrophobic substituent is a steroid derivative, the spacer molecule may be a bond of the carbamate $-N-C(O)-O-$ type, or alternatively when the hydrophobic substituent is a double-chain alkyl such as a dialkylamino for example, the spacer molecule may be chosen from the groups of formula -alkyl-C(O)—.

According to the present invention, a "therapeutic molecule" is a molecule that makes it possible to prevent or cure a pathology that manifests itself in the regions of the body producing an increased acidity compared with what is physiologically normal. Such regions are more specifically, but not solely:
  tumors, such as tumor cells and also normal cells in the vicinity of these tumors (for example the endothelial cells of the tumors), that exhibit a higher local acidity than what is, physiologically normal (N. Raghunand et al., Drug Resistance Updates, 2000, 3, pp. 30-38),
  muscles affected by ischemia, for example the cardiac muscle, wherein the acidosis partly results from the lactic acid produced by the anaerobic fermentation of hydrocarbons of the sugar type or of the fatty acids,
  the inflammation areas where the production of superoxide ions by the macrophages consumes a lot of oxygen,
  or alternatively the tissues where a metabolic, infectious or inflammatory disorder produces local acidosis.

According to another embodiment, the "therapeutic molecules" according to the present invention make it possible to prevent or cure a pathology by their release into an acidic cellular compartment, for example, into the endosome of the cells that is acidic.

The therapeutic molecules may thus be chosen, for example, from peptides, oligopeptides, proteins, antigens and their antibodies, enzymes and their inhibitors, hormones, antibiotics, analgesics, bronchodilators, antimicrobials, antihypertensive agents, cardiovascular agents, agents acting on the central nervous system, antihistamines, antidepressants, tranquilizers, anticonvulsants, anti-inflammatory substances, stimulants, antiemetics, diuretics, antispasmodics, antiischemics, agents limiting cell death, or alternatively anticancer agents.

In addition, a "biologically active substance" is a substance chosen either from the therapeutic molecules as defined above, or from nucleic acids.

According to the present invention, a "nucleic acid" is a deoxyribonucleic acid or a ribonucleic acid. This may include natural or artificial sequences, such as genomic DNA (gDNA), complementary DNA (cDNA), messenger RNA (mRNA), transfer RNA (tRNA), ribosomal RNA (rRNA), hybrid sequences or synthetic or semisynthetic sequences, oligonucleotides that are modified or otherwise. These nucleic acids may be, for example, of human, animal, plant, bacterial, viral or synthetic origin. They may be obtained by any technique known to persons skilled in the art, and in particular by screening libraries, by chemical synthesis, or alternatively by mixed methods including the chemical or enzymatic modification of sequences obtained by screening libraries. They may be modified chemically.

In addition, the deoxyribonucleic acids may be single or double-stranded as well as short oligonucleotides or longer oligonucleotides. Also, the nucleic acids comprise, for example, plasmids, vectors, episomes or expression cassettes. These deoxyribonucleic acids may also carry a replication origin that is functional in the target cell, at least one marker gene, at least one sequence for regulation of transcription or of replication, at least one gene of therapeutic interest, at least one antisense sequence that is modified or unmodified, or alternatively, at least one region for binding to other cellular components.

In one embodiment of the present invention, the nucleic acid comprises an expression cassette comprising at least one gene of therapeutic interest under the control of at least one promoter and of a transcriptional terminator that are active in the target cells.

According to the present invention, an "expression cassette for a gene of interest" is a DNA fragment that may be inserted into a vector at specific restriction sites. The DNA fragment comprises a nucleic acid sequence encoding an RNA or nucleic peptide of interest and comprises, in addition, the sequences necessary for the expression (activator(s), promoter(s), polyadenylation sequences and the like) of said sequence. The cassette and the restriction sites are designed to ensure insertion of the expression cassette into an appropriate reading frame for transcription and translation.

This generally includes a plasmid or an episome carrying at least one gene of therapeutic interest. By way of example, there may be mentioned the plasmids described in patent applications WO 96/26270 and WO 97/10343 incorporated into the present by reference.

According to the present invention, a "gene of therapeutic interest" is generally, any gene encoding a protein product having a therapeutic effect. The protein product thus encoded may be, for example, a protein or a peptide. This protein product may be exogenous, homologous or endogenous with respect to the target cell, that is to say a product that is normally expressed in the target cell when the latter exhibits no pathology. In this case, the expression of a protein makes it possible, for example, to compensate for an inadequate expression in the cell or the expression of an inactive or a weakly active protein because of a modification, or alternatively to overexpress said protein. The gene of therapeutic interest may also encode a mutant of a cellular protein, that has for example increased stability or a modified activity. The protein product may also be heterologous with respect to the target cell. In this case, an expressed protein can for example supplement or provide an activity that is deficient in the cell, allowing it to combat a pathology, or to stimulate an immune response.

Among the therapeutic products for the purposes of the present invention, there may be mentioned, for example, blood derivatives, hormones, lymphokines, interleukins, interferons or TNF (for example: FR 92/03120), growth factors, neurotransmitters or their precursors or synthesis enzymes, trophic factors (for example BDNF, CNTF, NGF, IGF, GMF, aFGF, bFGF, NT3, NT5, or alternatively HARP/pleiotrophin), apolipoproteins (for example ApoAI, ApoAIV, or ApoE: FR 93/05125), dystrophin or a minidystrophin (FR 91/11947), cystic fibrosis associated protein CFTR, tumor suppresser genes (for-example p53, Rb, Rap1A, DCC, or k-rev: FR 93/04745), genes encoding factors involved in coagulation (factors VII, VIII, IX), genes involved in DNA repair, suicide genes (thymidine kinase, cytosine deaminase), the genes for hemoglobin or other protein carriers, metabolic enzymes, catabolic enzymes and the like.

The nucleic acid of therapeutic interest may also be a gene or an antisense sequence, whose expression in the target cell makes it possible to control the expression of genes or the transcription of cellular mRNAs. Such sequences can, for example, be transcribed in the target cell into RNAs that are complementary to cellular mRNAs and thus block their translation to protein, according to the technique described in patent EP 140 308. The therapeutic genes also comprise the sequences encoding ribozymes, that are capable of selectively destroying target RNAs (EP 321 201).

As indicated above, the nucleic acid may also comprise at least one gene encoding an antigenic peptide, capable of generating an immune response in humans or animals. In this embodiment, the invention allows the production either of vaccines or of immunotherapeutic treatments applied to humans or animals, such as, for example, against microorganisms, viruses or cancer. This may include, for example, antigenic peptides specific for the Epstein-Barr virus, the HIV virus, the hepatitis B virus (EP 185 573), the pseudo-rabies virus, the syncitia forming virus, other viruses or alternatively antigenic peptides specific for tumors (EP 259,212).

In addition, the nucleic acid may also comprise sequences allowing the expression of the gene of therapeutic interest and/or of the gene encoding the antigenic peptide in the desired cell or organ. This may include, for example, sequences that are naturally responsible for the expression of the gene considered when these sequences are capable of functioning in the infected cell. This may also include, for example, sequences of a different origin (responsible for the expression of other proteins, or even synthetic). This may include promoter sequences of eukaryotic or viral genes. For example, this may include promoter sequences derived from the genome of the cell that it is desired to infect. Likewise, this may include promoter sequences derived from the genome of a virus. In this regard, there may be mentioned, for example, the promoters of the E1A, MLP, CMV and RSV genes and the like. In addition, these expression sequences may be modified by the addition of activating or regulatory sequences and the like. This may also include an inducible or repressible promoter.

Moreover, the nucleic acid may also comprise, for example, upstream of the therapeutic gene of interest, a signal sequence directing the therapeutic product synthesized in the secretory pathways of the target cell. This signal sequence may be the natural signal sequence of the therapeutic product, but it may also be any other functional signal sequence, or an artificial signal sequence. The nucleic acid may also comprise a signal sequence directing the therapeutic product synthesized toward a particular compartment of the cell.

According to one embodiment of the present invention, the acid-sensitive compounds may be chosen from the compounds of general formula:

wherein:

g is an integer equal to 0 or 1

G is a substituent chosen from the hydrogen atom, the alkyl substituents comprising 1 to 6 carbon atoms in the form of a saturated or unsaturated, straight or branched chain, or aryls, and $G_1$ and $G_2$ represent:

(a') one a hydrophilic substituent chosen from linear or branched alkyls comprising at least 3 carbon atoms and wherein at least one of the methylene groups may be replaced with an amino group that is optionally substituted (with a methyl group for example) and the terminal methyl(s) is(are) substituted with at least one group chosen from (primary, secondary, tertiary or quaternary) amines, guanidines or cyclic guanidines, and the other a hydrophobic substituent chosen from single- or double-chain alkyls or steroid derivatives, or alternatively (b') one a hydrophobic linear alkyl group comprising 10 to 24 carbon atoms and optionally comprising at least one unsaturation, and the other a group of general formula:

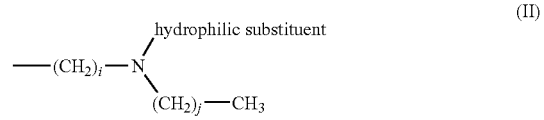

wherein i is an integer ranging from 1 to 4 and j is an integer ranging from 9 to 23, and the hydrophilic substituent is chosen from linear or branched alkyls comprising at least 3 carbon atoms and wherein at least one of the methylene groups may be replaced with an amino group that is optionally substituted (with a methyl group for example) and the terminal methyl(s) is(are) substituted with at least one group chosen from (primary, secondary, tertiary or quaternary) amines, guanidines or cyclic guanidines, or alternatively (c') one a hydrophilic substituent chosen from polyalkylene glycols and the other a substituent chosen from polyalkyleneimines, or alternatively (d') one a hydrophilic substituent chosen from polyalkylene glycols and the other a hydrophobic substituent chosen from single- or double-chain alkyls, steroid derivatives or the covalent conjugates between a single- or double-chain alkyl or a steroid derivative and a polyalkylene glycol molecule comprising 1 to 20 monomeric units, or alternatively (e') one a hydrophilic substituent chosen from polyalkylene glycols and the other a therapeutic molecule.

In another embodiment, the acid-sensitive compounds of the invention are chosen from the compounds of general formula:

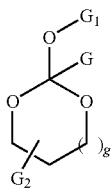

(I)

wherein:
g is an integer equal to 0 or 1
G represents a substituent chosen from the hydrogen atom, the alkyl substituents comprising 1 to 6 carbon atoms in the form of a saturated or unsaturated, straight or branched chain, or phenyl, and
$G_1$ and $G_2$ represent:

(a) one a hydrophilic substituent chosen from linear or branched alkyls comprising at least 3 carbon atoms and wherein at least one of the methylene groups may be replaced with an amino group that is optionally substituted (with a methyl group for example) and the terminal methyl(s) is(are) substituted with at least one group chosen from (primary, secondary, tertiary or quaternary) amines, guanidines or cyclic guanidines and the other a hydrophobic substituent chosen from single- or double-chain alkyls or steroid derivatives, or alternatively (d) one a hydrophilic substituent chosen from polyalkylene glycols and the other a hydrophobic substituent chosen from single- or double-chain alkyls or steroid derivatives.

The novel acid-sensitive compounds of general formula (I) may be provided in the form of nontoxic and pharmaceutically acceptable salts. These nontoxic salts comprise the salts with inorganic acids (hydrochloric, sulfuric, hydrobromic, phosphoric or nitric acids) or with organic acids (acetic, propionic, succinic, maleic, hydroxymaleic, benzoic, fumaric, methanesulfonic or oxalic acids).

The acid-sensitive compounds according to the present invention may be prepared according to many methods chosen from those described in the literature for the synthesis of molecules containing a cyclic ortho-ester group (for example, reference may be made to the examples given in the review Synthesis, Robert H. DeWolfe, 1974, pp. 153-172). According to one embodiment that can be envisaged, the acid-sensitive compounds of general formula (I) may, for example, be obtained by reacting an alcohol of formula $G_1OH$ with an ortho-ester of general formula:

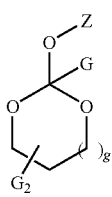

(III)

wherein g, G, $G_1$ and $G_2$ are as defined for the general formula (I), and Z represents a linear or branched alkyl group containing 1 to 4 carbon atoms.

This substitution may be carried out in the presence of an acid catalyst and/or may be heat activated at a temperature ranging from 50 and 150° C., with or without solvent. If it is chosen to carry out the procedure in the presence of a solvent, the latter is chosen from conventional organic chemistry solvents such as for example the organochlorinated solvents, aromatic solvents or alternatively ethers. When a catalyst is used, it may be an inorganic or organic acid, a Lewis or Brönsted acid. For example, the catalyst may be chosen from hydrochloric acid, sulfuric acid, para-toluenesulfonic acid, camphorsulfonic acid, pyridinium para-toluenesulfonate, or alternatively magnesium chloride. This substitution can also be favored by distilling the alcohol ZOH produced during the reaction if it is more volatile than the alcohol $G_1OH$. This continuous distillation may be carried out by heating at atmospheric pressure or under reduced pressure.

The starting alcohol $G_1OH$ is either commercially available, or it can be synthesized by any method known to persons skilled in the art, for example by hydration of the corresponding alkene, by hydrolysis of the corresponding halogenated derivative, or alternatively by reducing the corresponding carbonyl-containing derivative.

According to another variant of the invention, the group Z may already represent the group $G_1$ and in this case, the step for the reaction between the ortho-ester of general formula (III) and the alcohol $G_1OH$ is not necessary.

The compound of general formula (III) may be obtained by the action of a trialkyl ortho-ester of general formula (IV):

(IV)

wherein Z and G are as defined above, and $Z_1$ and $Z_2$, that are identical or different, represent linear or branched alkyl groups containing 1 to 4 carbon atoms, on a diol of general formula (V):

(V)

wherein g and $G_2$ are as defined above.

The reaction may be carried out according to conventional methods for protecting diols as ortho-ester, for example according to the methods indicated by T. W. Greene and P. G. M. Wuts in "Protective Groups in Organic Synthesis"($2^{nd}$ Ed., Wiley-Interscience, pp. 135-136). The procedure is generally carried out in a conventional organic solvent (for example organochlorinated solvents, aromatic solvents, ethers and the like) in the presence of an acid catalyst. The catalyst may be chosen from inorganic or organic acids, Lewis or Brönsted acids. For example, it is possible to use hydrochloric acid, sulfuric acid, para-toluenesulfonic acid, camphorsulfonic acid, pyridinium para-toluenesulfonate, or alternatively magnesium chloride.

The trialkyl ortho-ester of general formula (IV) is either commercially available, or it can be synthesized according to conventional methods known to persons skilled in the art, for example from the corresponding ester, or alternatively by substitution of the alkoxy groups starting with another commercial trialkyl ortho-ester.

The diol of general formula (V) is either commercially available, or can be obtained by the reaction between a commercial diol and $G_2$, or alternatively it can be obtained by direct functionalization of $G_2$ to a diol. This functionalization may for example consist in an oxidation of the corresponding alkene, or alternatively in the opening of a corresponding epoxide, according to methodologies well known to persons skilled in the art.

When either of $G_1$ and $G_2$ represents a substituent of the polyamine type (that is to say a linear or branched alkyl comprising at least 3 carbon atoms and wherein at least one of the methylene groups may be replaced with an amino group that is optionally substituted (with a methyl group for example) and the terminal methyl(s) is(are) substituted with at least one group chosen from (primary, secondary, tertiary or quaternary) amines, guanidines or cyclic guanidines, it is either commercially available, or it is obtained according to conventional methods known to persons skilled in the art or according to the methods described in the prior art (for example in the publications WO 96/17823, WO 97/18185, WO 98/54130 or alternatively WO 99/51581).

When either of $G_1$ and $G_2$ represents a hydrophobic substituent chosen from the single- or double-chain alkyls, the latter is either commercially available, or it is obtained according to conventional methods known to persons skilled in the art. For example, when this includes a dialkylamino substituent with a long carbon chain, it can be prepared from the corresponding primary amine by alkylation (monosubstitution of a halogenated alkyl), by alkylative reduction (from an aldehyde), or alternatively by condensation/reduction (formation of an amide function from an acid and then reduction).

When either of $G_1$ and $G_2$ represents a hydrophobic substituent chosen from the steroid derivatives or the hydrophobic dendrimers, it may be, for example, chosen from commercially available products.

When either of $G_1$ and $G_2$ represents a substituent chosen from polyalkylene glycols or mono- or polysaccharides, the latter is either commercially available, or it is obtained by conventional methods known to persons skilled in the art, such as by polymerization. In the case wherein the substituent is covalently linked to a targeting element, the synthesis of the acid-sensitive compounds according to the present invention described above can be carried out before or after the binding, by the conventional methods of persons skilled in the art, of said targeting element to this substituent.

When either of $G_1$ and $G_2$ represents a substituent chosen from polyalkyleneimines, the latter is either commercially available, or it is obtained according to the conventional methods known to a person skilled in the art or according to the methods described in the prior art, for example in the publication WO 96/02655.

The method of preparation indicated above constitutes only a method given by way of illustration, and any other equivalent method of preparation can naturally also be used. For example, it is possible to carry out the reactions starting with a diol of general formula (V) that does not possess the group $G_2$ but, in place, a functional group that is optionally protected (for example a protected amine), by carrying out an additional final step for the binding of the group $G_2$ (for example, deprotection of the amine and then condensation of the acid of formula $G_2COOH$).

Another subject of the invention relates to the compositions comprising at least one acid-sensitive compound of general formula (I) as defined above. According to a variant of the invention, said compositions comprise at least one biologically active substance and an acid-sensitive compound of general formula (I) wherein $G_1$ and $G_2$ have the definitions indicated under (a), (b), (c) or (d).

The compositions according to the invention may, in addition, comprise at least one adjuvant capable of binding with the complexes formed between the acid-sensitive compound according to the invention and the biologically active substance. In another embodiment, the present invention therefore relates to the compositions comprising at least one biologically active substance, an acid-sensitive compound of formula (I) wherein $G_1$ and $G_2$ have the definitions indicated under (a), (b), (c) or (d), and at least one adjuvant. The presence of this type of adjuvants (lipids, peptides or proteins for, example) can advantageously make it possible to increase the transfecting power of the compounds in the cases where the biologically active substance is a nucleic acid to be transfected.

In this perspective, the compositions according to the present invention may comprise, as adjuvant, at least one neutral lipid. It has indeed been shown that the addition of a neutral lipid makes it possible to improve the formation of the nucleolipid particles (in the case where the biologically active substance is a nucleic acid), and to promote the penetration of the particle into the cell by destabilizing its membrane.

In addition, said neutral lipids are, for example, lipids with two fatty chains. Natural or synthetic, zwitterionic lipids or lipids free of ionic charge under physiological conditions, may be advantageously used. They may be chosen, for example, from dioleoylphosphatidylethanolamine (DOPE), oleoylpalmitoylphosphatidyletanolamine (POPE), distearoylphosphatidylethanolamine (DSPE), dipalmitoyl-phosphatidylethanolamine (DPPE), dimirystoylphosphatidyl-ethanolamine (DMPE) as well as their derivatives that are N-methylated 1 to 3 times, phosphatidylglycerols, diacylglycerols, glycosyldiacylglycerols, cerebrosides (such as, for example, galactocerebrosides), sphingolipids (such as, for example, sphingomyelins) or alternatively asialogangliosides (such as, for example, asialoGM1 and GM2).

These various lipids may be obtained either by synthesis, or by extraction from organs (example: the brain) or from eggs, by conventional techniques well known to persons skilled in the art. For example, the extraction of the natural lipids may be carried out by means of organic solvents (see also Lehninger, Biochemistry).

In one embodiment of the present invention, in the case where the biologically active substance is a nucleic acid, the compositions of the invention comprise from 0.01 to 20 equivalents of adjuvant(s) for one equivalent of nucleic acids in mol/mol, such as, for example, from 0.5 to 5.

The acid-sensitive compounds according to the invention may have various uses depending on the substituents $G_1$ and $G_2$ situated on either side of the cyclic ortho-ester.

In the case where the substituents $G_1$ and $G_2$ have the definitions indicated in (a), (b) or (c) in the general formula (I), the acid-sensitive compounds according to the invention can form conjugates (for example of the type including liposomes, complexes or alternatively nanoparticles) directly with biologically active substances that may then be released into the tissues or cellular compartments, that are more acidic than what is physiologically normal. These acid-sensitive compounds are also useful for the transfection of nucleic acids. Such a use is illustrated in examples 7 and 8.

In the case-where the substituents $G_1$ and $G_2$ have the definitions indicated in (d) in formula (I), the acid-sensitive compounds according to the invention constitute nonionic surfactants that make it possible both to stabilize particles encapsulating a biologically active substance and to release said biologically active substance by degradation in the regions that are very weakly acidic to acidic in the body, such as, for example, regions where the pH is acidic and is between about 4 and about 7. Examples of the use of these acid-sensitive compounds is illustrated, for example, in examples 9 and 10.

In addition, the polysaccharide or polyalkylene glycol substituents, and including polyethylene glycol (PEG), are known to confer a sort of "furtiveness" on the particles with which they are associated by inhibiting the nonspecific adsorption by the serum proteins, and consequently the inhibiting recognition of said particles by macrophages (see for example Torchilin et al., Biochim. Biophys. Acta 1994, 1195, pp. 11-20 or Papahadjopoulos et al., PNAS 1991, 88, p. 11460-4). Thus, the acid-sensitive compounds comprising a PEG molecule according to the invention have an advantage from the safety point of view and also an additional advantage in the sense that they reduce the risk of interference with other proteins. At the level of the acidic regions in the body, the degradation of the ortho-ester present in the compounds according to the invention allows the separation of the PEG molecules from the rest of the particle, making the biologically active substance again "available" (there is in fact "disappearance of the furtiveness"). A selective transfer can thus be expected with respect to the acidic tissues.

Finally, in the case where the substituents $G_1$ and $G_2$ have the definitions indicated in (e) or (f) in the general formula (I), the acid-sensitive compounds according to the invention constitute covalent conjugates allowing the vectorization of a therapeutic molecule and then its release in the acidic regions of the body. These covalent conjugates are of the same type as those described by Kratz et al., but with a novel acid-sensitive bond between the therapeutic molecule and the "vector" part that has the advantage of having a modulable sensitivity compared with the pH-sensitive bonds used up until now.

Thus, the subject of the present invention is also the use of the acid-sensitive compounds of general formula (I) as defined above for the manufacture of a medicament intended for treating diseases. In this case, the disease targeted determines the choice of the biologically active substance.

According to embodiment of the present invention, when the biologically active substance is a nucleic acid, the acid-sensitive compounds of general formula (I) wherein $G_1$ and $G_2$ have the definitions indicated under (a), (b) or (c) can be used for the manufacture of a medicament intended for the in vitro, ex vivo or in vivo transfection of nucleic acids, such as, for example, into primary cells or into established lines. This may include, for example, fibroblast cells, muscle cells, nerve cells (neurons, astrocytes, glial cells), hepatic cells, cells of the hematopoietic line (lymphocytes, CD34, dendritic cells and the like), or alternatively epithelial cells, in differentiated or pluripotent form (precursors).

Finally, according to another alternative of the invention, the acid-sensitive compounds of general formula (I) wherein $G_1$ and $G_2$ have the definitions indicated under (e) or (f) can be used as a medicament.

In the preceding text, the acid-sensitive compounds according to the present invention become degraded in the tissues or cellular compartments whose pH is more acidic than what is physiologically normal. However, according to another alternative, it is possible to induce or to increase the acidity in the target region of the body by a general or local treatment known to persons skilled in the art. There may be mentioned by way of example, without limitation, the injection of an acidic product into the region to be treated or alternatively the intravenous injection of glucose that causes specific acidification of tumor tissues (T. Volk et al.; Br. J. Cancer; 1993, 68 (3), 492-500). Thus, the acid-sensitive compounds according to the present invention may also be used in regions of the body that are a priori nonacidic and that have been made acidic by treatments known to persons skilled in the art.

For all the uses of the acid-sensitive compounds according to the present invention indicated above, the compositions according to the invention comprising:

either an acid-sensitive compound of general formula (I) wherein $G_1$ and $G_2$ have the definitions indicated under (e) or (f), or an acid-sensitive compound of general formula (I) wherein $G_1$ and $G_2$ have the definitions indicated under (a), (b), (c) or (d) and a biologically active substance, can be formulated for administration, for example, by the topical, cutaneous, oral, rectal, vaginal, parenteral, intranasal, intravenous, intramuscular, subcutaneous, intraocular, transdermal, intratracheal or intraperitoneal route. In one embodiment of the present invention, the compositions of the invention contain a pharmaceutically acceptable vehicle for an injectable formulation, such as, for example, for a direct injection into the desired organ, or for administration by the topical route (to the skin and/or mucous membrane). This may include in particular isotonic, sterile solutions or dry, in particular freeze-dried compositions that, upon addition, depending on the case, of sterilized water or physiological saline, allow the preparation of injectable solutions. The doses of biologically active substances used for the injection as well as the number of administrations may be adjusted according to various parameters, and, for example, according to the mode of administration used, the relevant pathology, the chain to be expressed when the biologically active substance is a nucleic acid, or alternatively the desired duration of treatment. As regards to the mode of administration, this may include, for example, either a direct injection into the tissues, for example at the level of the tumors, or the circulatory pathways, or a treatment of cells in culture followed by their reimplantation in vivo, by injection or transplantation. The relevant tissues in the context of the present invention are for example the muscles, the skin, the brain, the lungs, the liver, the spleen, the bone marrow, the thymus, the heart, the lymph, blood, the bones, the cartilages, the pancreas, the kidneys, the bladder, the stomach, the intestines, the testicles, the ovaries, the rectum, the nervous system, the eyes, the glands or alternatively the connective tissues.

In addition to the preceding arrangements, the present invention also comprises other characteristics and advantages that will emerge from the examples and figures that follow, and that should be considered as illustrating the invention without limiting the scope thereof. For example, the Applicants propose, without limitation, various operating protocols as well as reaction intermediates that can be used to prepare the compounds of general formula (I). Of course, it is within the capability of persons skilled in the art to draw inspiration from these protocols and/or intermediate products in order to develop similar procedures so as to arrive at other compounds of general formula (I) according to the invention.

FIGURES

FIG. 1: Variation of the level of fluorescence as a function of time at pH 5 of complexes formed between DNA and a control cationic lipid or alternatively the acid-sensitive compounds A Syn or Trans, in 3 different ratios: 0.4 or 1.7 or 6.0 nmol of cationic lipid or of acid-sensitive compound/μg of DNA.

Figure 2:
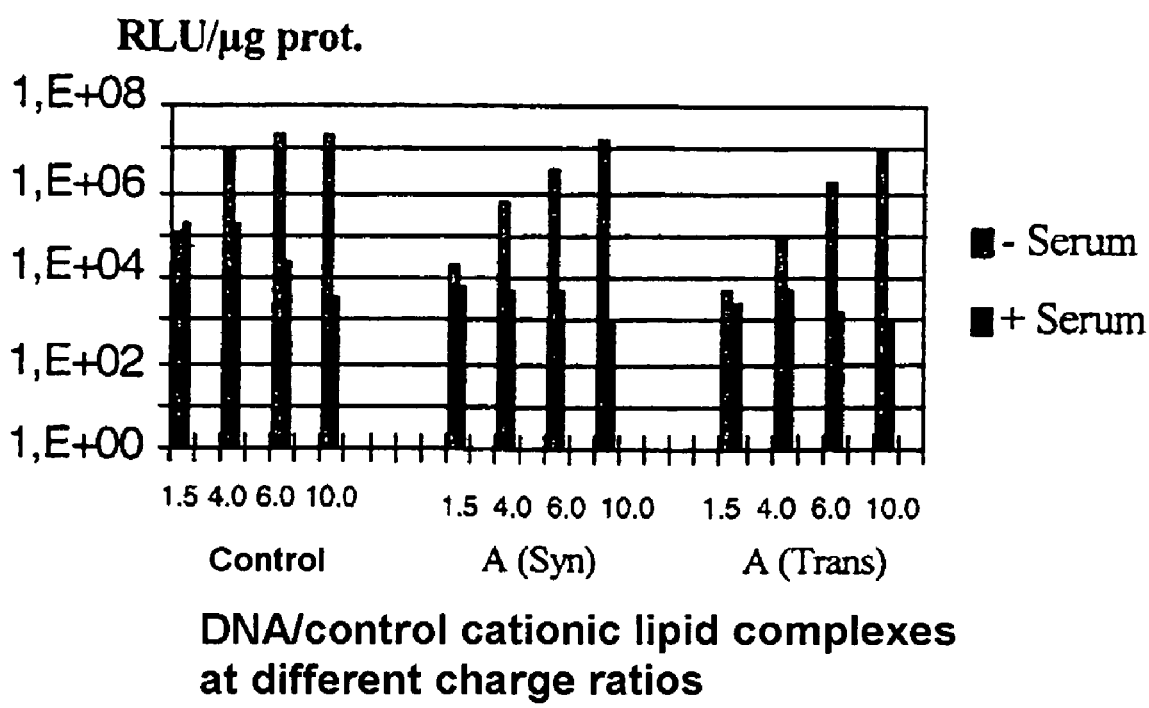

FIG. 2: Efficiency of transfection in vitro into HeLa cells of complexes formed between DNA and compound A Syn or Trans or a control cationic lipid, at different charge ratios, with or without serum. The y-axis represents the expression of luciferase in pg/well/μg of protein. The x-axis indicates the compound A Syn or Trans or control cationic lipid/DNA charge ratio.

Figure 3:
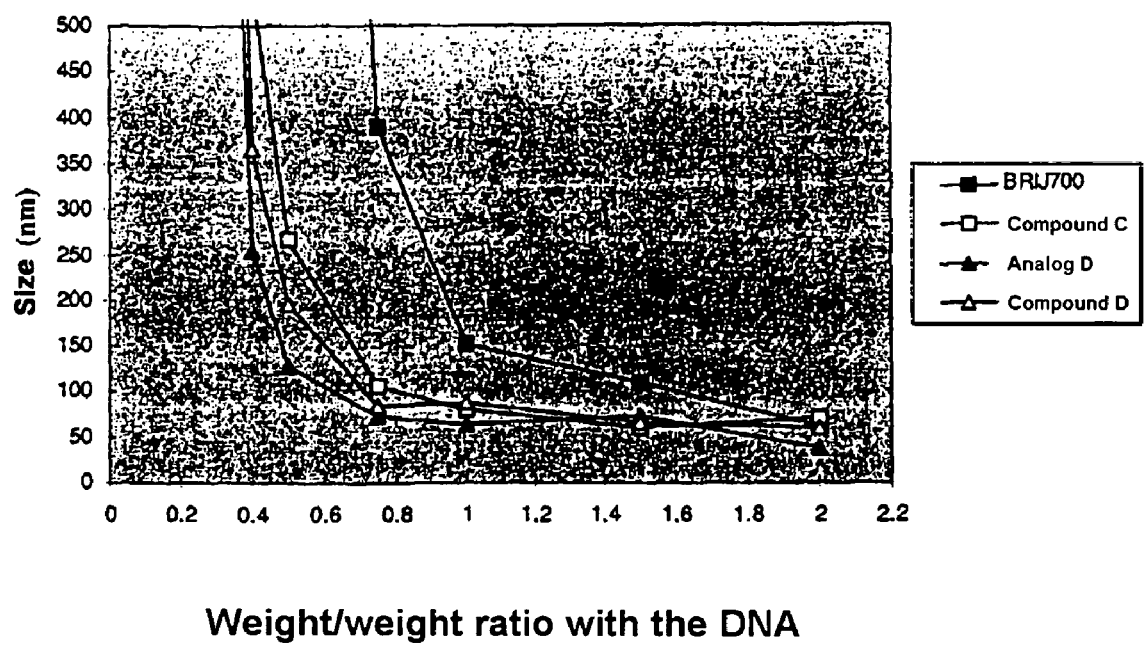

FIG. 3: Variation of the size (in nm) of control cationic lipid/DNA nucleolipid particles as a function of the quantity of compound C or compound D or of Brij700 (C18-PEG$_{5000}$, Sigma) or of a non-acid-sensitive analog of compound D (Analog D) used relative to the quantity of DNA (weight/weight). A small size indicates that the nucleolipid particles are stabilized. A very large size indicates on the contrary destabilization of the nucleolipid particles that then tend to aggregate.

Figure 4:
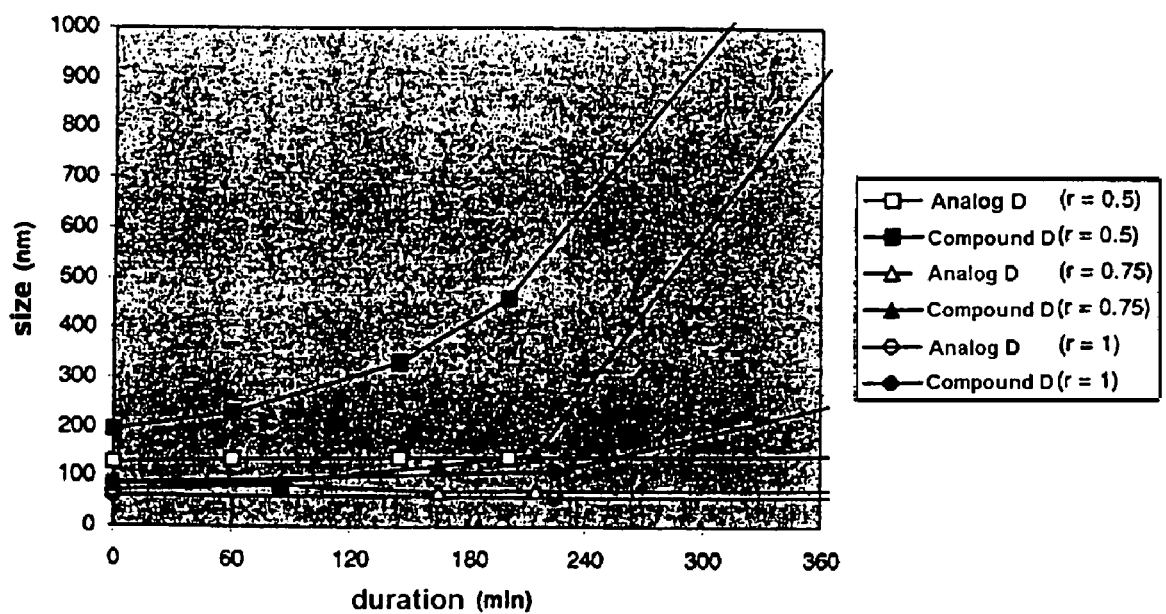

FIG. 4: Variation of the size (in nm) of control cationic lipid/DNA/compound or analog D nucleolipid particles as a function of time, at different ratios (weight/weight), when the pH is 5. A small size of the nucleolipid particles indicates that they are stabilized. A very large size indicates on the contrary destabilization of the nucleolipid particles that then tend to aggregate.

Figure 5:
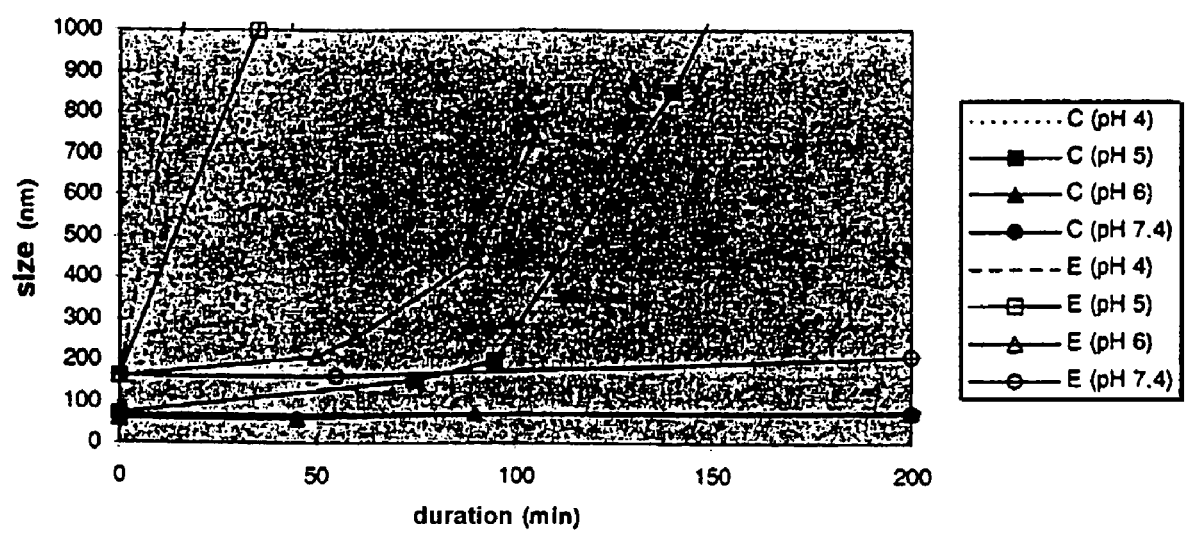

FIG. 5: Variation of the size (in nm) of control cationic lipid/DNA/compound C or compound E nucleolipid particles as a function of time, at various pH values (pH 4, pH 5, pH 6 and pH 7.4). The compound C or compound E/DNA ratio is set at 1 (in mmol/_g of DNA).

Figure 6:
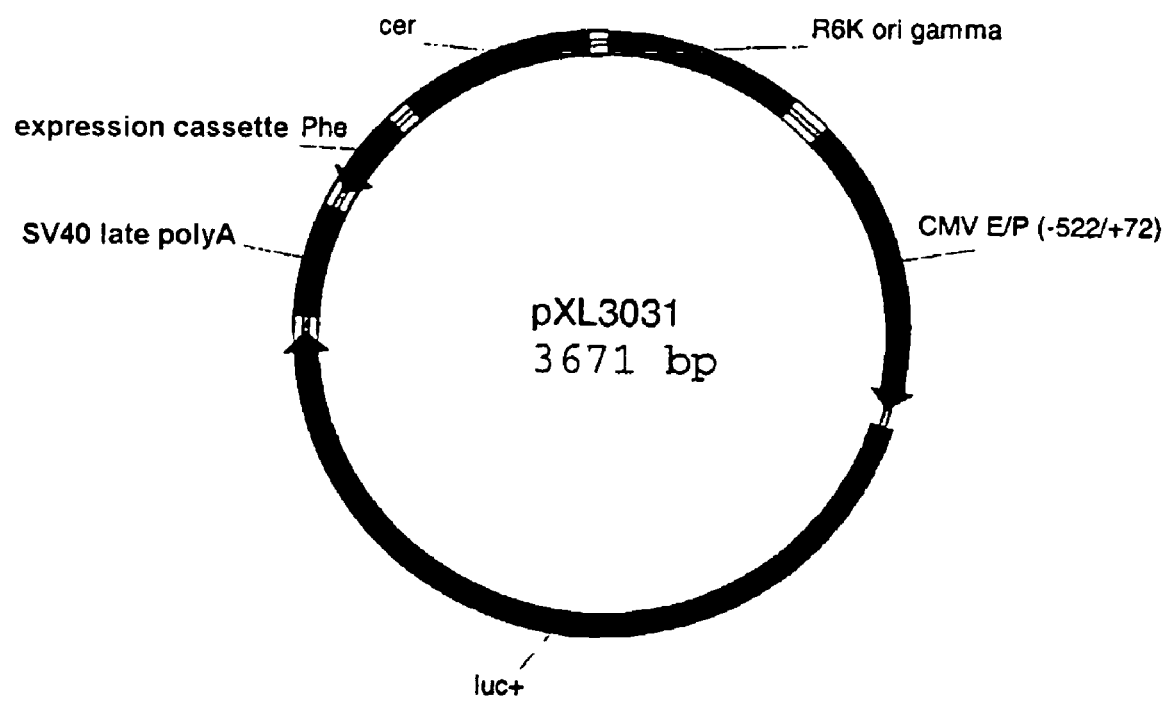

FIG. 6: Schematic representation of the plasmid pXL3031.

FIG. 7: Dose response of pH labile C18-PEG$_{5000}$ (Compound C) on gene transfer activity in vivo mediated by a cationic lipid/DOPE/DNA (5/5/1) complex. Non-degradable C18-PEG$_{5000}$ (BRIJ700) was used as a negative control. Data are mean (lines) and individual values of 4 Balb/C mice bearing subcutaneous M109 tumor.

FIG. 8: Dose response of pH labile cholesterol-PEG$_{5000}$ (Compound D) on gene transfer activity in vivo mediated by a cationic lipid/DOPE/DNA (5/5/1) complex. Non-degradable cholesterol-PEG$_{5000}$ (Analog D) was used as a negative control. Data are mean (lines) and individual values of 4 Balb/C mice bearing subcutaneous M109 tumor.

EXAMPLES

Reagents and catalysts such as triethylamine, trifluoroacetic acid, trifluoroacetic anhydride, tert-butyl bromoacetate, butyrolactone, 3-aminopropan-1,3-diol, serinol(2-aminopropan-1,3-diol), trimethyl ortho-formate, trimethyl ortho-acetate, para-toluenesulfonic acid, pyridinium para-toluenesulfonate or alternatively benzotriazol-1-yloxytris(dimethylamino)phosphonium (BOP) hexafluorophosphate, were generally commercially available.

The washings were performed with aqueous solutions saturated with sodium chloride, saturated with sodium hydrogen carbonate and with a concentrated solution of potassium hydrogen sulfate at 0.5 mol/l.

The hydrophilic polymers (polyethylene glycols of different sizes) were commercially available. The hydrophilic substituents of the polyamine type were also commercially available or alternatively they were synthesized by conventional methods known to a person skilled in the art as indicated, for example, in the examples that follow. The hydrophobic substituents (single- or double-chain dialkylamines, fatty alcohols and the like) were commercially available or alternatively synthesized according to conventional methods known to a person skilled in the art. For example, the single- or double-chain dialkylamines may be synthesized from primary amines and the corresponding halogenated alkyl derivatives as indicated in the examples that follow.

The Proton Nuclear Magnetic Resonance ($^1$H NMR) spectra were recorded on Bruker 300, 400 and 600 MHz spectrometers. The clinical shifts were expressed in ppm (part per million) and the multiplicities by the usual abbreviations.

The plasmid used was pXL3031 described in the publication Gene Therapy (1999) 6, pp, 1482-1488, that contains the luc gene encoding luciferase under the control of the cytomegalovirus CMV E/P promoter. This plasmid is represented in FIG. 6. Its size was 3671 bp. The plasmid solution used was diluted to 1.262 g/l in water for injection.

Example 1

Synthesis of 2,2,2-trifluoro-N-(2-methoxy-[1,3]dioxolan-4-ylmethyl)acetamide ("Ortho 1")

2,2,2-Trifluoro-N-(2-methoxy-[1,3]dioxolan-4-ylmethyl)acetamide ("Ortho 1") has the formula:

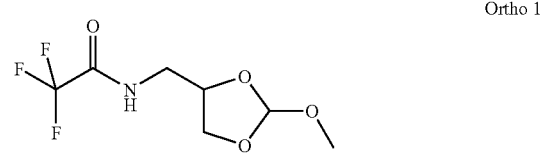

Ortho 1

It was obtained in -two steps from 3-aminopropan-1,2-diol:

1) Preparation of N-(2,3-dihydroxypropyl)-2,2,2-trifluoroacetamide 15 g of 3-aminopropan-1,2-diol (164.6 mmol) were solubilized in 100 ml of tetrahydrofuran in a round-bottomed flask provided with a magnetic bar. The reaction mixture was then cooled to 0° C. on an ice bath and 21.5 ml of ethyl trifluoroacetate (181.1 mmol) were gradually added. The reaction mixture was stirred for 2 hours at room temperature. The crude reaction product was then evaporated to dryness. 29 g of a pure colorless oil were thus obtained (yield: 95%), that product was used without further purification.

2) Preparation of 2,2,2-trifluoro-N-(2-methoxy-[1,3] dioxolan-4-ylmethyl)acetamide (ortho 1)

The 29 g of N-(2,3-dihydroxypropyl)-2,2,2-trifluoroacetamide obtained in the preceding step (155 mmol) were solubilized in 75 ml of dichloromethane supplemented with 75 ml of trimethyl ortho-formate (685 mmol). 300 mg of para-toluenesulfonic acid (1.7 mmol) were then added and the reaction mixture was stirred for 2 hours at room temperature.

This crude product was then diluted in 500 ml of dichloromethane, washed with 3 times 200 ml of saturated sodium hydrogen carbonate and then 3 times 200 ml of saturated sodium chloride. The organic phase was dried over magnesium sulfate, filtered and concentrated to dryness. 30 g of a pure oily product were thus obtained (yield: 85%) without further purification.

$^1$H NMR (300 MHz, CDCl$_3$, δ in ppm). A mixture of two diastereoisomers in the proportions 50/50 was observed.

*3.33 and 3.37 (2s: 3H in total); from 3.35 to 3.80 (mts: 3H); from 4.10 to 4.25 (mt: 1 H); 4.50 (mt: 1 H); 5.73 and 5.78 (2s: 1H in total); 6.66 and 7.55 (2 unresolved complexes: 1H in total).

Example 2

Synthesis of 2,2,2-trifluoro-N-(2-methoxy-2-methyl-[1,3]dioxan-5-yl)acetamide ("Ortho 2")

2,2,2-Trifluoro-N-(2-methoxy-2-methyl-[1,3]dioxan-5-yl)acetamide ("Ortho 2") has the formula:

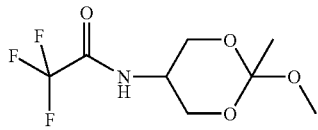

Ortho 2

It was obtained in two steps from 2-aminopropan-1,3-diol (serinol):

1) Preparation of 2,2,2-trifluoro-N-(2-hydroxy-1-hydroxymethylethyl)acetamide 4 g of 2-aminopropan-1,3-diol (43.9 mmol) were supplemented with 20 ml of tetrahydrofuran. The reaction mixture was then cooled to 0° C. on an ice bath and 5.8 ml of ethyl trifluoroacetate (48.3 mmol) were gradually added. This solution was stirred for 2 hours at room temperature.

The reaction mixture was then evaporated to dryness, taken up 3 times in dichloromethane so as to completely evaporate the tetrahydrofuran. 8.1 g of white powder (yield: 99%) were obtained pure and used in the next step without further purification.

2) Preparation of 2,2,2-trifluoro-N-(2-methoxy-2-methyl-[1,3]dioxan-5-yl)acetamide (Ortho 2)

7.9 g of 2,2,2-trifluoro-N-(2-hydroxy-1-hydroxymethylethyl)acetamide obtained in the preceding step (42.2 mmol) were solubilized in 30 ml of dichloromethane supplemented with 16.1 ml of trimethyl ortho-acetate (126.7 mmol). 73 mg of para-toluenesulfonic acid (0.42 mmol) were then added and the reaction mixture was stirred for 3 hours at room temperature.

The crude reaction product was then diluted with 150 ml of dichloromethane, washed with 3 times 50 ml of a saturated sodium hydrogen carbonate solution, and then 3 times 50 ml of a saturated sodium chloride solution. The organic phase was dried over magnesium sulphate, filtered and concentrated to dryness. 9.9 g of a white solid were obtained pure without further purification (yield: 96%).

$^1$H NMR (300 MHz, CDCl$_3$, δ in ppm). A mixture of two diastereoisomers in the approximate proportions 75/25 was observed.

*1.49 and 1.50 (2 s: 3H in total); 3.34 and 3.35 (2 s: 3H in total); 3.66 and 3.82 (respectively dmt, J=12 Hz and dd, J=11 and 8 Hz: 2H in total); from 3.90 to 4.00 and from 4.20 to 4.35 (2 mts: 1 H in total); 3.97 and 4.33 (respectively dd, J=11 and 5 Hz and dmt, J=12 Hz: 2H in total); 6.38 and 7.04 (2 broad unresolved complexes: 1H in total).

Example 3

Synthesis of the Syn and Trans Compounds 4-{4-[(2-{3-[4-(3-amino-propylamino)butylamino]propyl-amino}acetylamino)methyl]-[1,3]dioxolan-2-yloxy}-N,N-dioctadecylbutyramide tetraacetate This example describes the route for the synthesis of the acid-sensitive compound A in the form of its two distinct diastereoisomeric forms Syn and Trans of formula:

Compound A

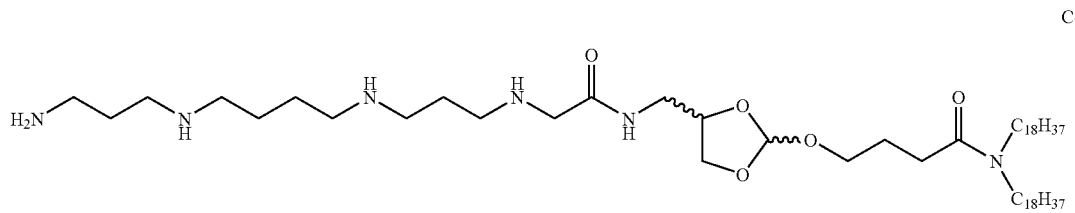

a—Synthesis of the Syn and Trans 4-(4-aminomethyl-[1,3]dioxolan-2-yloxy)-N,N-dioctadecylbutyramide (Lipid Portion-O-ortho 1-NH$_2$)

This synthesis was carried out in three stages: functionalization of the dioctadecylamine to an alcohol and attachment onto the group Ortho 1 whose protecting group was then cleaved.

1) Preparation of 4-hydroxy-N,N-dioctadecylbutyramide 4.6 g of aluminium chloride (34 mmol) were supplemented with 25 ml of chloroform, the whole being cooled to about 10° C. on a thermostated bath. 6.4 ml of triethylamine (46 mmol) in 15 ml of chloroform were added dropwise and then the reaction mixture was allowed to return to room temperature. 6 g of dioctadecylamine (11.5 mmol), mixed with 1 ml of butyrolactone (13.8 mmol) in 110 ml of chloroform, were gradually added to the mixture using a dropping funnel.

The reaction no longer changed after magnetical stirring for 2 hours at room temperature. 75 ml of water were then added and the reaction mixture was stirred for 30 minutes. The crude product was filtered on Celite and then washed with chloroform. The filtrate was separated by settling out and the organic phase was washed with 3 times 50 ml of a saturated sodium chloride solution. The chloroformic solution was dried over magnesium sulfate, filtered and concentrated. 4.9 g of a white powder were obtained after chromatography on silica (yield: 70%).

2) Preparation of the Syn and Trans N,N-dioctadecyl-4-{4-[2,2,2-trifluoroacetylamino)methyl]-[1,3]dioxolan-2-yloxy}butyramides 2.8 g of 4-hydroxy-N,N-dioctadecylbutyramide obtained in the preceding step (4.6 mmol) were mixed with 2.6 g of 2,2,2-trifluoro-N-(2-methoxy-[1,3]dioxolan-4-ylmethyl)acetamide (Ortho 1, 11.5 mmol) and 90 mg of magnesium chloride (0.92 mmol). The whole was heated without solvent at 80° C. for two hours.

The crude reaction product was then dissolved in 150 ml of cyclohexane and washed with 3 times 30 ml of a saturated sodium hydrogen carbonate solution, and then with 3 times 30 ml of a saturated sodium chloride solution. The organic phase was dried over magnesium sulfate, filtered and concentrated. The purification was carried out by chromatography on silica. 1.2 g and 1.1 g of the two expected diastereoisomers Syn and Trans were thus isolated in the form of a white powder (yield: 62%).

$^1$H NMR for the compound SYN (300 MHz, CDCl$_3$, δ in ppm): 0.89 (t, J=7 Hz: 6H); from 1.15 to 1.40 (mt: 60H); 1.52 (mt: 4H); 1.94 (mt : 2H); 2.39 (t, J=7 Hz: 2H); 3.20 (broad t, J=8 Hz: 2H); 3.29 (mt: 2H); 3.61 (t, J=5 Hz: 2H); 3.66 (mt: 2H); 3.79 (dd, J=8 and 7 Hz: 1H); 4.11 (t, J=8 Hz: 1H); 4.50 (mt: 1H); 5.82 (s: 1H); 8.13 (unresolved complex: 1H).

$^1$H NMR for the compound TRANS (300 MHz, CDCl$_3$, δ in ppm): 0.89 (t, J=7 Hz: 6H); from 1.15 to 1.40 (mt: 60H); 1.52 (mt: 4H); 1.95 (mt: 2H); 2.38 (t, J=7 Hz: 2H); 3.21 (broad t, J=8 Hz: 2H); 3.29 (broad t, J=8 Hz: 2H); 3.44 (mt, 1H); from 3.55 to 3.75 (mt: 1H); 3.60 (t, J=6 Hz: 2H); 3.69 (dd, J=8.5 and 5 Hz: 1H); 4.19 (dd, J=8.5 and 7 Hz: 1H); 4.50 (mt: 1H); 5.87 (s, 1H); 6.70 (unresolved complex: 1H).

3) Preparation of the Syn and Trans 4-(4-aminomethyl-[1,3]dioxolan-2-yloxy)-N,N-dioctadecylbutyramide 1.1 g of N,N-dioctadecyl-4-{4-[(2,2,2-trifluoroacetylamino)methyl]-[1,3]dioxolan-2-yloxy}butyramide obtained in the preceding step (1.37 mmol, Syn or Trans) were dissolved in 10 ml of tetrahydrofuran and 10 ml of molar sodium hydroxide at 4% were added, with vigorous stirring. The reaction was left overnight at room temperature.

The tetrahydrofuran was then concentrated and then the product was extracted with three times 150 ml of diethyl ether. The organic phase was dried over calcium chloride, filtered and evaporated. 840 mg of the expected products were thus isolated (yield: 86%), and used as they were for the next step.

b—Synthesis of (trifluoroacetyl-{3-[trifluoroacetyl-(4-{trifluoroacetyl-[3-(2,2,2-trifluoroacetylamino)-propyl]amino}butyl)amino]propyl}amino)acetic acid (hydrophilic part polyamine-COOH)

This synthesis was performed in two steps: protection of the four amines of the spermine and then substitution of one of the primary amines with the protected bromoacetic acid.

1) Synthesis of 2,2,2-trifluoro-N-[3-(2,2,2-trifluoroacetylamino)propyl]-N-(4-{trifluoroacetyl-[3-(2,2,2-trifluoroacetylamino)propyl]amino}-butyl)acetamide 8 g of spermine (39.5 mmol) were solubilized in 75 ml of dichloromethane. 33 ml of triethylamine (237 mmol) were added and then the reaction mixture was cooled to 0° C. on an ice bath. 41.5 g of trifluoroacetic anhydride diluted in 100 ml of dichloromethane were then added dropwise over 1 hour using a dropping funnel. The reaction mixture was then allowed to return to room temperature and the reaction was left overnight with stirring.

75 ml of a 5% sodium hydrogen carbonate solution were then added to the reaction mixture and the solution was stirred for 15 minutes at room temperature. The aqueous phase was extracted with 3 times 150 ml of dichloromethane. The organic phases were combined and washed with 3 times 100 ml of a concentrated potassium hydrogen sulfate solution at 0.5 M, and then 3 times 100 ml of a saturated sodium chloride solution. The organic phase was then dried over magnesium sulfate, filtered and concentrated to dryness. 22.5 g of a pure yellow powder were isolated without further purification (yield: 97%).

2) Preparation of (trifluoroacetyl-{3-[trifluoroacetyl-(4-{trifluoroacetyl-[3-(2,2,2-trifluoroacetylamino)-propyl]amino}butyl)amino]propyl}amino)acetic acid 1 g of sodium hydride (60% in oil, that was 25.6 mmol) were supplemented with 60 ml of dry dimethylformamide. The reaction mixture, under an argon stream, was cooled on a water bath and then 10 g of the 2,2,2-trifluoro-N-[3-(2,2,2-trifluoroacetylamino)-propyl]-N-(4-{trifluoroacetyl-[3-(2,2,2-trifluoro-acetylamino)propyl]amino}butyl)acetamide obtained above (17 mmol), solubilized in 40 ml of dry dimethylformamide, were added dropwise. The reaction mixture was left for 1 hour at room temperature and then was again cooled on an ice bath and 3.66 g of tert-butyl bromoacetate (18.7 mmol) were added. The reaction mixture was stirred overnight at room temperature.

500 ml of ethyl acetate were then added and then the mixture was washed with three times 100 ml of a saturated sodium hydrogen carbonate solution, and three times 100 ml of a saturated sodium chloride solution. The organic phase was then dried over magnesium sulfate, filtered and concentrated to dryness. A yellow oil containing the expected impure product was thus isolated in the form of a tert-butyl ester.

This crude reaction product was diluted in 50 ml of dichloromethane and 50 ml of trifluoroacetic acid were added. The solution was stirred for 3 hours at room temperature. The reaction mixture was then evaporated to dryness and then diluted in 50 ml of dichloromethane. The product was then extracted with 3 times 150 ml of a saturated sodium hydrogen carbonate solution. The aqueous phase obtained was washed with 3 times 30 ml of dichloromethane and was then acidified by addition of concentrated hydrochloric acid. The product was then extracted with 3 times 300 ml of dichloromethane. The organic phase was dried over magnesium sulfate, filtered and concentrated to dryness. The purification was continued by chromatography on silica (elution: dichloromethane/methanol 8/2). 3.5 g of a yellow powder were thus recovered (total yield over the two steps: 32%).

$^1$H NMR (400 MHz, (CD$_3$)$_2$SO d6 at a temperature of 373K, δ in ppm): 1.62 (mt: 4H); from 1.80 to 2.00 (mt: 4H); 3.28 (mt: 2H); from 3.30 to 3.60 (mt: 10H); 4.01 (s: 2H); from 9.15 to 9.35 (unresolved complex: 1H).

c—Synthesis of the Syn and Trans 4-{4-[(2-{3-[4-(3-aminopropylamino)butylamino]propylamino}acetylamino)-methyl]-[1,3]dioxolan-2-yloxy}-N,N-dioctadecyl-butyramides tetraacetate (acid-sensitive compound A)

This synthesis was performed in three steps: condensation of the two molecules whose synthesis has just been described in a and b, and then deprotection of the polyamine and finally salification. The same protocol was used for the products Syn and Trans.

1) Synthesis of the Syn and Trans N,N-dioctadecyl-4-(4-{[2-(trifluoroacetyl-{3-[trifluoroacetyl-(4-{trifluoro-acetyl-[3-(2,2,2-trifluoroacetylamino)propyl]amino}-butyl)amino]propyl}amino)acetylamino]methyl}-[1,3]-dioxolan-2-yloxy)butyramides 800 mg of 4-(4-aminomethyl-[1,3]dioxolan-2-yloxy)-N,N-dioctadecylbutyramide (1.13 mmol Syn or Trans) obtained above (step a) dissolved in 10 ml of dichloromethane were successively supplemented with 390 µl of triethylamine (2.8 mmol), 800 mg of (trifluoroacetyl-{3-[trifluoroacetyl-(4-{trifluoro-acetyl-[3-(2,2,2-trifluoroacetylamino)propyl]amino}-butyl)amino]propyl}amino)acetic acid (1.24 mmol) obtained above in step b and 600 mg of BOP. The solution was stirred for 2 hours at room temperature.

The crude reaction product was then concentrated, taken up in 150 ml of ethyl acetate, washed with three times 40 ml of a saturated sodium hydrogen carbonate solution and then three times 40 ml of a saturated sodium chloride solution. After drying over magnesium sulfate, filtration and evaporation, the product was purified by chromatography on silica (elution: ethyl acetate). 1.1 g of white powder were thus isolated (yield: 73%).

2) Preparation of the Syn and Trans 4-{4-[(2-{3-[4-(3-aminopropylamino)butylamino]propylamino}acetylamino)-methyl]-[1,3]dioxolan-2-yloxy}-N,N-dioctadecyl-butyramides 290 mg of N,N-dioctadecyl-4-(4-{[2-(trifluoroacetyl-{3-[trifluoroacetyl-(4-{trifluoro-acetyl-[3-(2,2,2-trifluoro-acetylamino)propyl]amino}-butyl)amino]propyl}amino)acetylamino]methyl}-[1,3]-dioxolan-2-yloxy)butyramide (0.22 mmol, Syn or Trans) that were obtained above were dissolved in 3 ml of tetrahydrofuran, and 3 ml of molar sodium hydroxide at 4% were added with vigorous stirring. The reaction was left overnight at room temperature.

The solvent was then concentrated and then the crude product was taken up in a dichloromethane/methanol 1/1 mixture. This crude solution was purified by chromatography on silica (dichloromethane/methanol/ammonia, 45/45/10). The product was concentrated and then freeze-dried after addition of water. 180 mg of white freeze-dried product were thus obtained (yield: 87%).

3) Preparation of the Diastereoisomers Syn and Trans of 4-{4-[(2-{3-[4-(3-aminopropylamino)butylamino]propyl-amino}acetylamino)methyl]-[1,3]dioxolan-2-yloxy}-N,N-dioctadecylbutyramide (compound A)

The product obtained in the preceding step, in the form of a free base, was then quantitatively salified on an ion-exchange resin: it was solubilized in a water/ethanol mixture and was eluted in a column containing a large excess of acetate resin (BIO-RAD; AG 1-X2 Resin).

$^1$H NMR for the compound SYN (400 MHz, CDCl$_3$, δ in ppm): 0.89 (t, J=7 Hz: 6H); from 1.20 to 1.40 (mt: 60H); 1.52 (mt: 4H); from 1.65 to 1.90 (mt: 8H); 1.93 (mt: 2H); 1.97 (s: 3H); 2.37 (t, J=7 Hz: 2H); 2.73 (mt: 4H); 2.81 (t, J=6.5 Hz: 2H); 2.89 (mt: 4H); 2.95 (t, J=6.5 Hz: 2H); from 3.15 to 3.30 (mt: 4H); 3.32 (AB, J=17 Hz: 2H); 3.45 (dt, J=14 and 6.5 Hz: 1H); from 3.55 to 3.65 (mt: 1H); 3.61 (split t, J=7 and 2 Hz: 2H); 3.74 (t, J=8 Hz: 1H); 4.06 (t, J=8 Hz: 1H); 4.31 (mt: 1H); 5.79 (s: 1H), 7.81 (t, J=5.5 Hz: 1H).

$^1$H NMR for the compound TRANS (400 MHz, CDCl$_3$, δ in ppm): 0.88 (t, J=7 Hz: 6H); from 1.05 to 1.45 (mt: 60H); 1.51 (mt: 4H); from 1.65 to 1.90 (mt: 8H); 1.92 (mt: 2H); 1.97 (s: 3H); 2.37 (t, J=7 Hz: 2H); 2.73 (mt: 4H); 2.80 (t, J=6 Hz: 2H); 2.88 (mt: 4H); 2.96 (t, J=6 Hz: 2H); from 3.15 to 3.55 (mt: 8H); 3.57 (broad t, J=6 Hz: 2H); 3.69 (dd, J=7.5 and 5.5 Hz: 1H); 4.11 (t, J=7.5 Hz: 1H); 4.43(mt: 1H); 5.85 (s, 1H); 7.73 (broad t, J=5.5 Hz: 1H).

Example 4

Synthesis of 4-{4-[(2-{3-[bis(3-aminopropyl)amino]propylamino}acetylamino)methyl]-[1,3]dioxolan-2-yloxy}-N,N-ditetradecylbutyramide tetrachlorohydride This example describes a route of synthesis of the acid-sensitive compound B, in the form of an equimolar mixture of the two diastereoisomers Syn and Trans, of formula:

Compound B

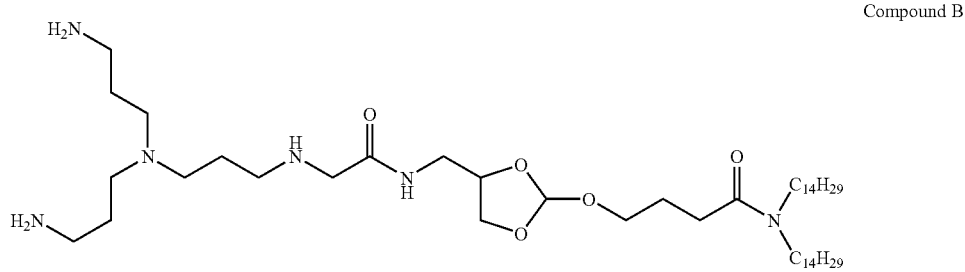

a—Synthesis of 4-(4-aminomethyl-[1,3]dioxolan-2-yloxy)-N,N-ditetradecylbutyramide (Lipid Part-O-Ortho 1-NH$_2$)

This synthesis was performed in four steps: synthesis of the ditetradecylamine that was then functionalized to an alcohol and then attached to the group Ortho 1 whose protecting group was then cleaved.

1) Ditetradecylamine Hydrochloride 74 g of bromotetradecane (267.1 mmol) were supplemented with 400 ml of ethanol and 57 g of tetradecylamine (267.1 mmol). 70.8 g of sodium carbonate (667 mmol) were then placed in suspension and the reaction mixture was heated under reflux overnight. The reaction mixture was then evaporated to dryness, taken up in 1.5 l of dichloromethane and washed with 3 times 200 ml of water and then once 400 ml of a saturated sodium chloride solution. The organic phase was dried over calcium chloride and concentrated.

The salification was carried out by solubilization of the crude product in the hot state in 600 ml of isopropanol supplemented with 300 ml of 5 N hydrochloric acid in isopropanol. The clear solution thus obtained was allowed to cool, that induced crystallization of the expected product. 48.4 g of flocculant white powder were obtained after filtration and washing with isopropanol (yield: 41%).

2) Preparation of 4-hydroxy-N,N-ditetradecylbutyramide 22.4 g of aluminum chloride (168.1 mmol) were supplemented with 75 ml of chloroform, the whole being cooled to about 10° C. on an ice-cold water bath. 39 ml of triethylamine (280.1 mmol) in 100 ml of chloroform were added dropwise and then the reaction mixture was allowed to return to room temperature. 25 g of ditetradecylamine hydrochloride (56 mmol) mixed with 5.2 ml of butyrolactone (67.2 mmol) in 350 ml of chloroform were gradually added to the mixture, with mechanical stirring. The reaction no longer changed after 2 hours at room temperature.

200 ml of water were then added and the reaction mixture was stirred for 30 minutes. The crude product was filtered on Celite and then washed with chloroform. The filtrate was separated after settling out and the organic phase was washed with three times 150 ml of a saturated sodium chloride solution. The chloroformic solution was dried over magnesium sulfate, filtered and concentrated. 21.2 g of white powder were obtained with a yield of 76% after chromatography on silica (ethyl acetate/cyclohexane 1/1).

3) Preparation of N,N-ditetradecyl-4-{4-[(2,2,2-trifluoroacetylamino)methyl]-[1,3]dioxolan-2-yloxy}butyramide 3.5 g of 4-hydroxy-N,N-ditetradecylbutyramide (7.1 mmol) obtained in the preceding step were mixed with 1.8 g of 2,2,2-trifluoro-N-(2-methoxy-[1,3]dioxolan-4-ylmethyl)acetamide (Ortho 1, 7.8 mmol) and 18 mg of pyridinium para-toluenesulfonate (PPTS, 0.071 mmol). The whole was heated without solvent at 80° C. for 3 hours.

The crude reaction product was then dissolved in 200 ml of heptane, washed with 3 times 50 ml of a saturated sodium hydrogen carbonate solution, with 3 times 50 ml of acetonitrile and was then concentrated to dryness.

A small fraction of the crude product was purified on silica in order to characterize this intermediate, the remainder was used as it was for the next step. The chromatography on silica (cyclohexane/ethyl acetate 7/3 V/V) allowed us to isolate a few mg of oily product.

4) Preparation of 4-(4-aminomethyl-[1,3]dioxolan-2-yloxy)-N,N-ditetradecylbutyramide The crude product obtained in the preceding step was solubilized in 20 ml of tetrahydrofuran supplemented with 20 ml of sodium hydroxide at 4%. The reaction mixture was left overnight with vigorous stirring at room temperature.

The tetrahydrofuran was then concentrated and then the product was extracted with 3 times 200 ml of diethyl ether. The organic phase was dried over calcium chloride, filtered and evaporated. Chromatography on silica (dichloromethane/methanol 9/1 V/V) made it possible to isolate 1.6 g of a colorless oil (yield on the two steps: 38%).

$^1$H NMR (300 MHz, CDCl$_3$, δ in ppm): a mixture of two diastereoisomers in the proportions 50/50 was observed.

*0.89 (t, J=7 Hz: 6H); from 1.15 to 1.45 (mt: 44H); 1.52 (mt: 4H); 1.58 (unresolved complex: 2H); 1.95 (quintuplet, J=6.5 Hz: 2H); 2.39 (t, J=6.5 Hz: 2H); from 2.75 to 3.00 (mt: 2H); 2.31 (mt: 2H); 3.29 (mt: 2H); 3.60 (mt: 2H); 3.71 and 3.80 (respectively dd, J=7.5 Hz and 6 Hz and t, J=7.5 Hz: 1H in total); 4.06 and 4.14 (2 t, J=7.5 Hz: 1H in total); 4.21 and 4.33 (2 mts: 1H in total); 5.82 and 5.85 (2 s: 1H in total).

b—Synthesis of [(3-{bis[3-(2,2,2-trifluoroacetylamino)propyl]amino}propyl)trifluoroacetylamino] acetic acid in the form of a trifluoroacetate salt (hydrophilic part of the polyamine-COOH type)

The proposed synthesis was performed in 6 steps starting with 3-aminopropanol and 3,3'-iminobispropylamine.

1) Preparation of 2,2,2-trifluoro-N-{3-[3-(2,2,2-trifluoroacetylamino)propylamino]propyl}acetamide 35 g of 3,3'-iminobispropylamine (266.7 mmol) were solubilized in 150 ml of anhydrous tetrahydrofuran under an argon stream. The reaction mixture was then cooled to 0° C. on an ice bath and 65 ml of ethyl trifluoroacetate (546.8 mmol) were added dropwise (very slowly) using a dropping funnel. At the end of the addition (3 hours later), the reaction mixture was allowed to return to room temperature and the stirring was maintained for a few hours under argon.

The reaction mixture was then filtered on paper. The filtrate was concentrated to dryness, taken up several times in dichloromethane, the final drying being carried out in an oven at 40° C. under the vacuum produced by a slide vane rotary vacuum pump for 16 hours. 85.3 g of a white powder were isolated pure without further purification (yield: 99%).

2) Preparation of tert-butyl(3-hydroxypropylamino)-acetate 196 ml of 3-aminopropanol (2.56 mol) were diluted in 250 ml of dichloromethane and the whole was cooled to 0° C. on an ice bath. 20 g of tert-butyl bromoacetate (102.5 mmol), solubilized in 200 ml of dichloromethane, were then added dropwise while the reaction mixture was maintained at 0° C. At the end of the addition (2 hours later), the reaction mixture was left at room temperature for 3 hours.

This crude product was then washed with 3 times 150 ml of a saturated sodium hydrogen carbonate solution, and then 3 times 150 ml of a saturated sodium chloride solution. The organic phase was dried over calcium chloride, filtered and concentrated. 17.8 g of a colorless oil were thus isolated (yield: 92%).

3) Preparation of tert-butyl [(3-hydroxypropyl)-trifluoroacetylamino]acetate 17.65 g of tert-butyl (3-hydroxypropyl-amino)acetate (93.3 mmol) were solubilized in 100 ml of dichloromethane and the whole was cooled to 0° C. on an ice bath. 26 ml of triethylamine (186.6 mmol) were added, followed by a dropwise addition of 21.5 g of trifluoroacetic anhydride (102.6 mmol) using a dropping funnel. At the end of the addition, the reaction mixture was left at room temperature overnight, with magnetic stirring.

This solution was then washed with 3 times 50 ml of a saturated sodium hydrogen carbonate solution, 3 times 50 ml of a 0.5 M potassium hydrogen sulfate solution, and then 3 times 50 ml of a saturated sodium chloride solution. The organic phase was dried over magnesium sulfate, filtered and concentrated. 24.5 g of a pale yellow oil were thus isolated (yield: 92%).

4) Preparation of tert-butyl[(3-bromopropyl)trifluoro-acetylamino]acetate 10 g of tert-butyl [(3-hydroxypropyl)-trifluoroacetylamino]acetate (35 mmol) were solubilized in 150 ml of tetrahydrofuran. 12.4 g of triphenylphosphine (47.3 mmol) were added and the reaction mixture was thermostated at 15-20° C. 15.1 g of carbon tetrabromide (45.6 mmol), dissolved in 60 ml of acetonitrile, were added dropwise using a dropping funnel and the whole was stirred at room temperature for 4 hours.

The reaction mixture was then concentrated to dryness, taken up in ethyl acetate and filtered on paper. The filtrate was concentrated to dryness, taken up in cyclohexane and filtered on sintered material No. 3. The filtrate was again concentrated and purified by chromatography on silica (cyclohexane/ethyl acetate 8/2 V/V). 10.4 g of a pale yellow oil were thus isolated (yield: 85%).

5) Preparation of tert-butyl [(3-{bis[3-(2,2,2-trifluoroacetylamino)propyl]amino}propyl)trifluoro-acetylamino]acetate 26 g of tert-butyl [(3-bromopropyl)trifluoro-acetylamino]acetate (74.7 mmol). and 24.1 g of 2,2,2-trifluoro-N-{3-[3-(2,2,2-trifluoroacetylamino)propylamino]propyl}acetamide (74.7 mmol) were solubilized in 130 ml of acetonitrile. 30 g of potassium carbonate (224 mmol) were then placed in suspension and the whole was heated under reflux for 6 hours.

The reaction mixture was then filtered on paper and concentrated to dryness. The crude product was then purified by chromatography on silica (cyclohexane/ethyl acetate 2/8 V/V). 16.6 g of a pale yellow oil (yield: 38%) were thus isolated.

6) Preparation of the Trifluoroacetate Salt of [(3-{bis[3-(2,2,2-trifluoroacetylamino)propyl]amino}-propyl)trifluoroacetylamino]acetic acid 15.8 g of tert-butyl [(3-{bis[3-(2,2,2-trifluoroacetylamino)propyl]amino}propyl)trifluoro-acetylamino]acetate (28.76 mmol) were supplemented with 50 ml of dichloromethane and then with 50 ml of trifluoroacetic acid. This mixture was stirred for a few hours at room temperature. The reaction mixture was then concentrated to dryness. 18.7 g of pale yellow honey were thus isolated (yield: 100%).

$^1$H NMR (300 MHz, CDCl$_3$, δ in ppm): at room temperature, a mixture of rotamers was observed.

*from 1.80 to 2.10 (mt: 6H); 3.12 (mt: 6H); 3.29 (mt: 4H); 3.50 (mt: 2H); 4.13 and 4.29 (respectively broad s and mt: 2H in total); from 9.50 to 9.75 (mt: 2H)

c—Synthesis of 4-{4-[(2-{3-[bis(3-aminopropyl)amino]-propylamino}acetylamino)methyl]-[1,3]dioxolan-2-yloxy}-N,N-ditetradecylbutyramide tetrahydrochloride (compound B)

This synthesis was performed in three steps: condensation of the two molecules obtained in parts a and b above, and then deprotection of the polyamine and salification.

1) Preparation of 4-[4-({2-[(3-{bis[3-(2,2,2-trifluoroacetylamino)propyl]amino}propyl)trifluoroacetylamino]-acetylamino}methyl)-[1,3]dioxolan-2-yloxy]-N,N-ditetradecylbutyramide 1.9 ml of triethylamine (13.8 mmol), 2 g of [(3-{bis[3-(2,2,2-trifluoroacetylamino)propyl]amino}-propyl)trifluoroacetylamino]acetic acid (trifluoroacetate salt, 3.04 mmol) and 1.8 g of BOP (4.14 mmol) were successively added to 1.65 g of 4-(4-aminomethyl-[1,3]dioxolan-2-yloxy)-N,N-ditetradecylbutyramide (2.76 mmol) dissolved in 30 ml of dichloromethane. The solution was stirred for 1 hour at room temperature.

The crude reaction product was then concentrated to dryness, taken up in 200 ml of ethyl acetate, washed with 40 ml of a saturated sodium chloride solution, and then 3 times 40 ml of a saturated sodium hydrogen carbonate solution, and then 3 times 40 ml of a saturated sodium chloride solution. The product was then purified by chromatography on silica (elution: ethyl acetate). 2.2 g of pale yellow honey were thus isolated (yield: 72%).

2) Preparation of 4-{4-[(2-{3-[bis(3-aminopropyl)-amino]propylamino}acetylamino)methyl]-[1,3]dioxolan-2-yloxy}-N,N-ditetradecylbutyramide 2.1 g of 4-[4-({2-[(3-{bis[3-(2,2,2-trifluoroacetylamino)propyl]amino}propyl)trifluoro-acetylamino]acetylamino}methyl)-[1,3]dioxolan-2-yloxy]-N,N-ditetradecylbutyramide (1.88 mmol) were dissolved in 30 ml of tetrahydrofuran, and 30 ml of molar sodium hydroxide at 4% were added, with vigorous stirring. The reaction was left overnight at room temperature.

The solvent was then concentrated and then the crude product was taken up in a dichloromethane/methanol 1/1 mixture. This crude solution was purified by chromatography on silica (dichloromethane/methanol/ammonia, 45/45/10, V/V). The product was concentrated and then freeze-dried after addition of water. 1.3 g of white freeze-dried product were thus obtained (yield: 84%).

3) Preparation of 4-{4-[(2-{3-[bis(3-aminopropyl)amino]propylamino}acetylamino)methyl]-[1,3]dioxolan-2-yloxy}N,N-ditetradecylbutyramide tetrahydrochloride (compound B)

The product obtained in the preceding step in the form of a free base was then quantitatively salified on an ion-exchange resin: it was solubilized in water, and eluted in a column containing a large excess of chloride resin (FLUKA; DOWEX 21K). The structure of the white freeze-dried product obtained was confirmed by $^1$H NMR.

$^1$H NMR (300 MHz, (CD$_3$)$_2$SO d6, δ in ppm): a mixture of two diastereoisomers in the proportions 50/50 was observed.

*0.89 (t, J=7 Hz: 6H); from 1.15 to 1.40 (mt: 44H); from 1.40 to 1.60 (mt: 4H); 1.72 (mt: 8H); 2.31 (mt: 2H); from 2.40 to 2.55 (mt: 6H); from 2.70 to 2.90 (mt: 6H); from 3.15 to 3.75- from 4.00 to 4.40 (2 series of mt: 13H in total); 5.83 and 5.86 (2 s: 1H in total).

Example 5

Synthesis of the PEGoylated Lipids C and D

This example describes a route of synthesis of the pegoylated lipids Octadecanol-Ortho 1-PEG$_{5000}$-OMe and Cholesterol-Ortho 1-PEG$_{5000}$-OMe that differ from each other only in their lipid portion: octadecanol for compound C and cholesterol for compound D. These two acid-sensitive compounds have the general formula:

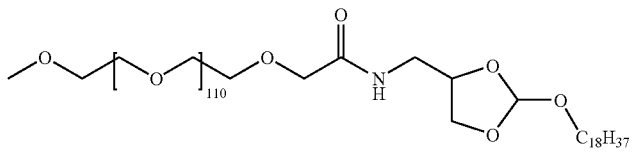

Compound C

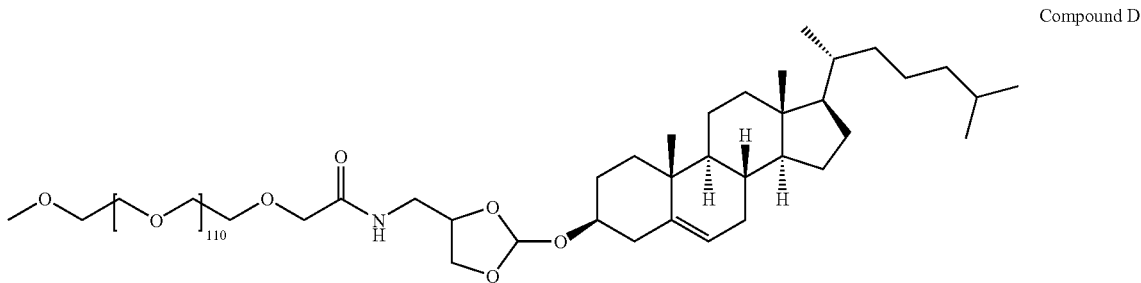

Compound D a—Synthesis of C-(2-octadecyloxy-[1,3]dioxolan-4-yl)methylamine and of C-{2-[17-(1,5-dimethylhexyl)-10,13-dimethyl-2,3,4,7,8,9,10,11,12,13,14,15,16,17-tetradecahydro-1H-cyclopenta[a]phenanthren-3-yloxy]-[1,3]dioxolan-4-yl}methylamine (lipid parts —O-Ortho 1-$NH_2$)

This synthesis was performed in two steps starting with the compound Ortho 1 by substitution of the exocyclic methoxy group with the fatty alcohol (cholesterol or octadecanol) and then deprotection of the amine.

1) Preparation of 2,2,2-trifluoro-N-(2-octadecyloxy-[1,3]dioxolan-4-ylmethyl)acetamide 3 g of 2,2,2-trifluoro-N-(2-methoxy-[1,3]dioxolan-4-ylmethyl)acetamide (Ortho 1, 13.09 mmol) were mixed with 3.54 g of octadecanol (13.09 mmol). The mixture was melted at 80° C. and left for 2 hours after the addition of 32 mg of pyridinium para-toluenesulfonate (0.13 mmol). The crude reaction product was then dissolved in cyclohexane, washed with a saturated sodium hydrogen carbonate solution and then with a saturated sodium chloride solution, dried over magnesium. sulfate and then concentrated to dryness. This crude product was used as it was for the next step.

1') Preparation of N-{2-[17-(1,5-dimethylhexyl)-10,13-dimethyl-2,3,4,7,8,9,10,11,12,13,14,15,16,17-tetradecahydro-1H-cyclopenta[a]phenanthren-3-yloxy]-[1,3]dioxolan-4-ylmethyl}-2,2,2-trifluoroacetamide The protocol was identical to that described above, it was possible for the reaction to also be performed without catalyst.

2) Preparation of C-(2-octadecyloxy-[1,3]dioxolan-4-yl)methylamine 6.12 g of crude reaction product of the preceding step 1 (13.09 mmol) were dissolved in 20 ml of tetrahydrofuran. The reaction mixture was cooled on an ice bath, and 30 ml of sodium hydroxide at 4% were added. The mixture was stirred at room temperature until complete disappearance of the reagent was obtained (over a period of 4 hours).

Next, the solvent was concentrated in part and then extracted with 3 times 200 ml of diethyl ether. The organic phase was dried over calcium chloride, filtered and evaporated. The crude reaction product was purified by chromatography on silica (dichloromethane/methanol 9/1, V/V). 2.6 g of a white powder were thus recovered (yield: 53% on the two consecutive steps 1 and 2).

$^1$H NMR (300 MHz, $CDCl_3$, δ in ppm). A mixture of two diastereoisomers in the approximate proportions 50/50 was observed.

*0.89 (t, J=7 Hz: 3H); from 1.20 to 1.45 and 1.58 (2 mts: 32H in total); from 2.75 to 3.00 (mt: 2H); 3.53 (mt: 2H); from 3.65 to 3.85 (mt: 1H); from 4.00 to 4.40 (mt: 2H); 5.81 and 5.84 (2 s: 1H in total).

2') Preparation of C-{2-[17-(1,5-dimethylhexyl)-10,13-dimethyl-2,3,4,7,8,9,10,11,12,13,14,15,16,17-tetradecahydro-1H-cyclopenta[a]phenanthren-3-yloxy]-[1,3]dioxolan-4-yl}methylamine The protocol was identical to that of step 2). 1.4 g of white powder were thus recovered (yield: 22% on the two consecutive steps 1' and 2').

$^1$H NMR (400 MHz, $CDCl_3$, δ in ppm). A mixture of two diastereoisomers in the approximate proportions 50/50 was observed. *0.69 (s: 3H); from 0.85 to 1.75-1.86 and 2.00 (mts: 26H in total); 0.88 (mt: 6H); 0.93 (d, J=7 Hz: 3H); 1.01 (s: 3H); 2.33 (mt: 2H); from 2.75 to 3.00 (mts: 2H); 3.50 (mt: 1H); 3.71-3.85-4.05 and 4.16 (4 mts: 2H in total); 4.20 and 4.35 (2 mts: 1H in total); 5.36 (mt: 1H); 5.93 and 5.96 (2 s: 1H in total).

b—Synthesis of the Acid of methoxypolyethylene glycol 5000 (hydrophilic part MeO-$PEG_{5000}$-COOH)

A single step was necessary: oxidation of the terminal hydroxyl group of the commercial methoxypolyethylene glycol.

20 g of MeO-$PEG_{5000}$-OH (4 mmol) were dissolved in 100 ml of an equal volume water/acetonitrile mixture. 312 mg of 2,2,6,6-tetramethylpiperidinyloxy (2 mmol) and then 6.4 g of

[bis(acetoxy)iodo]benzene (20-mmol) were added and the reaction mixture was left stirring for 16 hours at room temperature.

This crude reaction product was then evaporated to dryness, taken up in 40 ml of a dichloromethane/ethanol (1/1; V/V) mixture, and then precipitated by addition of 500 ml of diethyl ether. 19 g of a white powder were thus isolated by filtration and washing with ether (yield: 95%).

$^1$H NMR (300 MHz, CDCl$_3$, δ in ppm): 3.39 (s: 3H); from 3.40 to 3.95 (mts: 404H); 4.15 (s: 2H).

c—Synthesis of methoxy-(polyethylene glycol 5000)-(N-(2-octadecytoxy-[1,3]dioxolan-4-ylmethyl) amide (compound C) and of methoxy-(polyethylene glycol 5000)-N-{2-[17-(1,5-dimethylhexyl)-10,13-dimethyl-2,3,4,7,8,9,10,11,12,13,14,15,16,17-tetradecahydro-1H-cyclopenta[a]-phenanthren-3-yloxy]-[1,3]dioxolan-4-ylmethyl}amide (Compound D) Compound C 1.2 g of MeO-PEG$_{5000}$-COOH (0.24 mmol) obtained in the preceding steps were dissolved in 5 ml of dichloromethane. 188 μl of triethylamine (1.34 mmol) were added and then 100 mg of C-(2-octadecyloxy-[1,3]dioxolan-4-yl)methylamine (0.27 mmol). 143 mg of BOP (0.32 mmol, 1.2 eq) were then added and the reaction was left stirring at room temperature for one hour.

The reaction mixture was precipitated by addition of diethyl ether (60 ml), centrifuged, washed with ether and then injected into preparative high-performance liquid chromatography (HPLC). By isolating the purest fractions, 415 mg of white freeze-dried product were thus obtained (yield: 32%).

$^1$H NMR (300 MHz, CDCl$_3$, δ in ppm): a mixture of two diastereoisomers in the approximate proportions 50/50 was observed.

*0.90 (t, J=7 Hz: 3H); from 1.20 to 1.40 and from 1.50 to 1.75 (mts: 32H); 3.39 (s 3H); from 3.40 to 3.95 (mts: 448H); 4.02 and 4.03 (2s: 2H in total); from 4.00 to 4.25 (mts: 3H in total); 5.80 and 5.84 (2s: 1H in total).

Compound D:

The protocol was identical to that presented for the preparation of compound C. By isolating the purest fractions, 395 mg of white freeze-dried product were thus obtained (yield: 30%).

$^1$H NMR (400 MHz, CDCl$_3$, δ in ppm): a mixture of two diastereoisomers in the approximate proportions 50/50 was observed.

*0.68 (s: 3H); from 0.85 to 1.75-1.85 and 2.00 (mts: 26H in total); 0.87 (mt: 6H); 0.92 (d, J=7 Hz: 3H); 1.00 (s: 3H); 2.33 (mt: 2H); 3.39 (s: 3H); from 3.40 to 3.90 (mts: 448H); from 4.00 to 4.20 (mts: 1H in total); 4.01 and 4.04 (2s: 2H in total); 4.28 and 4.46 (2 mts: 1 H in total); 5.35 (mt: 1H); 5.90 and 5.95 (2s: 1H in total).

Example 6

Synthesis of the PEGoylated Lipid E

This example describes a route of synthesis of the pegoylated lipid octadecanol-Ortho 2-PEG$_{5000}$-OMe that has the general formula:

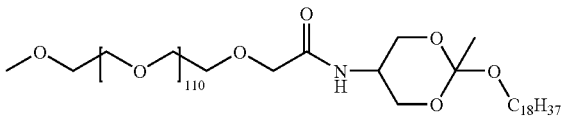

Compound E a—Synthesis of 2-methyl-2-octadecyloxy-[1,3]dioxan-5-ylamine (hydrophobic lipid part —O-Ortho2-NH$_2$)

This synthesis if performed in two steps started with the substrate Ortho 2 whose synthesis was described above, by substitution of the exocyclic methoxy group with octadecanol and then deprotection of the amine.

1) Preparation of 2,2,2-trifluoro-N-(2-methyl-2-octadecyloxy-[1,3]dioxan-5-yl)acetamide 3 g of 2,2,2-trifluoro-N-(2-methoxy-2-methyl-[1,3]dioxan-5-yl)acetamide (12.34 mmol) were mixed with 3 g of octadecanol (11.1 mmol). The mixture was melted at 80° C. and left for 2 hours in order to evaporate all the methanol produced during the alcohol exchange.

The molten reaction mixture was then poured into 50 ml of acetonitrile, that induced its precipitation. The expected product was purified by recrystallization from acetonitrile. 2.85 g of white powder were thus isolated (yield: 53% after recrystallization).

2) Preparation of 2-methyl-2-octadecyloxy-[1,3]dioxan-5-ylamine 1 g of the trifluoroacetamide derivative of the preceding step (2.08 mmol) was dissolved in 10 ml of tetrahydrofuran, to that 10 ml of molar sodium hydroxide at 4% were added. The mixture was vigorously stirred at room temperature until complete disappearance of the reagent was obtained (over a period of 4 hours).

Next, the solvent was concentrated in part and then extracted with 3 times 100 ml of diethyl ether. The organic phase was dried over calcium chloride, filtered and evaporated to dryness. 810 mg of white powder were thus isolated without purification (yield: 100%).

$^1$H NMR (400 MHz, CDCl$_3$, δ in ppm): 0.89 (t, J=7 Hz: 3H); from 1.20 to 1.50 (mt: 30H); 1.49 (s: 3H); 1.62 (mt: 2H); 1.67 (broad s: 2H); 2.71 (mt: 1 H); 3.46 (t, J=7 Hz: 2H); 3.54 (broad d, J=10 Hz: 2H); 4.30 (dd, J=10 and 1.5 Hz: 2H).

b—Synthesis of methoxy-(polyethylene glycol 5000)-N-(2-methyl-2-octadecyloxy-[1,3]dioxan-5-yl)amide (Compound E)

The last step consists in condensing the lipid amine with the acid of PEG (whose synthesis was described in example 5).

1.15 g of MeO-PEG$_{5000}$-COOH (0.23 mmol) were dissolved in 5 ml of dichloromethane. 181 μl of triethylamine (1.30 mmol) were added and then 100 mg of 2-methyl-2-octadecyloxy-[1,3]dioxan-5-ylamine (0.26 mmol). 172 mg of BOP (0.39 mmol) were then added and the reaction was left stirring at room temperature for one hour.

The reaction mixture was precipitated by addition of diethyl ether (60 ml), centrifuged, washed with ether and then injected into preparative HPLC. By isolating the purest fractions, 420 mg of white freeze-dried product were thus obtained (yield: 34%).

$^1$H NMR (400 MHz, CDCl$_3$, δ in ppm); 0.89 (t, J=7 Hz: 3H); from 1.20 to 1.50 (mt: 30H); 1.48 (s: 3H); from 1.55 to 1.75 (mt: 2H); 3.39 (s: 3H); from 3.40 to 3.90 (mt: 448H); 3.89 (broad d, J=8.5 Hz: 1H); 4.05 (s: 2H); 4.30 (broad d, J=12 Hz: 2H); 7.57 (d, J=8.5 Hz: 1H).

Example 7

Study of the Compaction of DNA by the Acid-Sensitive Compounds A Syn and Trans

The acid-sensitive compounds A forms Syn and Trans prepared above have a structure analogous to the cationic lipids conventionally used for the nonviral transfection of DNA, and they possess, inter alia, in their structure a cyclic ortho-ester function that contributes to making them acid-sensitive.

The aim of this example was therefore to demonstrate that the acid-sensitive compounds A Syn and Trans preserve the power to compact DNA to be transfected specific to the cationic lipids, while having the capacity to become degraded in acidic medium and therefore to release the compacted DNA. This was easily shown by a fluorescence test with ethidium bromide (EtBr): the absence of fluorescence reflects the absence of free DNA, that means that the DNA was compacted.

In the text that follows, the two forms Syn and Trans of the acid-sensitive compound A as prepared in example 3 were used and the non-acid-sensitive analog described in the publication WO 97/18185, and that has the formula:

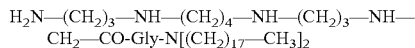

was used as control. This non-acid-sensitive analog was called in the text that follows "control cationic lipid".

The DNA was brought into contact with increasing quantities of control cationic lipid or of acid-sensitive compound A Syn or Trans, by mixing an equal volume of lipid solutions of different titers with the DNA solutions. Samples of 800 μl of DNA complexes having a concentration of 10 μg/μl were thus prepared in a sodium chloride solution at 150 mM with increasing quantities of control cationic lipid or of acid-sensitive compound A Syn or Trans.

At time t=0, 200 μl of buffer having a concentration of 0.1 mol/l at pH 5 were added to these samples and the samples were stored in an oven at 37° C. The fluorescence with ethidium bromide (EtBr) was measured over time (measurement at 20° C.) using a FluoroMax-2 (Jobin Yvon-Spex), with excitation and emission wavelengths of 260 nm and 590 nm respectively. The slit widths for excitation and for emission were set at 5 nm. The fluorescence value was recorded after addition of 3 μl of ethidium bromide at 1 g/l per ml of DNA/cationic lipid or DNA/acid-sensitive compound solution (at 0.01 mg of DNA/ml).

The results were summarized in FIG. 1. At pH 5, when the quantity of acid-sensitive compound A Syn or Trans or of control cationic lipid used to compact the DNA was too low (0.4 nmol lipid/pg of DNA) and when the DNA was therefore not completely compacted, no significant variation in fluorescence was measurable over time. On the other hand, a different behavior of the acid-sensitive compounds A Syn and Trans was observed with respect to the (non-acid-sensitive) control cationic lipid for larger quantities (1.7 nmol lipid/μg of DNA and 6.0 nmol lipid/μg of DNA) that allow complete compaction of the DNA. Indeed, the acid-sensitive compounds A Syn and Trans released the DNA over time as demonstrated by the increase in fluorescence, that was not the case with the control cationic lipid that was not acid-sensitive. It was observed, in addition, that this release of DNA occurred a few hours after the addition of acid (at pH 5 and 37° C.).

A shift was also observed in the kinetics of release of the DNA according to the quantity of acid-sensitive compound used: the lower the quantity of acid-sensitive compound A used, the more rapid the release of the DNA.

This study demonstrates the remarkable properties of the acid-sensitive compounds A Syn and Trans: they were capable of forming complexes with DNA by compacting it, and their degradation in acidic medium caused a degradation of the complexes formed with the DNA, and therefore the release of the DNA. These acid-sensitive compounds were therefore useful in the context of the nonviral transfection of DNA into cells.

Example 8

Study of the Transfecting Power of the Acid-Sensitive Compounds A Syn and Trans in Vitro This example illustrates the in vitro transfecting power of the acid-sensitive compounds A Syn and Trans, compared with their non-acid-sensitive analog described in the preceding example (the control cationic lipid).

This study was carried out at 4 different charge ratios: 1.0 or 4.0 or 6.0 or 10.0 nmol of lipid/μg of DNA. Each of these conditions was tested with and without fetal calf serum (A+ or − Serum a))

Culture of the cells: HeLa cells (American Type Culture Collection (ATCC) Manassas, Va., USA) derived from a human cervical epithelium carcinoma, were cultured in the presence of a medium of the MEM ("minimum essential medium") type with addition of 2 mM L-glutamine, 50 units/ml of penicillin, and 50 units/ml of streptomycin. The medium and the additives were obtained from Gibco/BRL Life Technologies/InvitroGen (Gaithersburg, Md., USA). The cells were cultured in flasks at 37° C. and at 5% carbon dioxide in an incubator.

Transfection: a day before the transfection, the HeLa cells were transferred into 24-well plates with a cell number of 30,000 to 50,000 per well. These dilutions represent approximately 80% confluence after 24 hours.

For the transfection, the cells were washed twice and incubated at 37° C. with 500 μl of medium with serum (10% FCS v/v) or without serum.

50 μl of complexes containing 0.5 μg of plasmid DNA were added to each well (the complexes were prepared at least 30 minutes before the addition to the well). After two hours at 37° C., the plates without serum were supplemented with 10% (v/v) of FCS ("Fetal Calf Serum").

All the plates were placed for 36 hours at 37° C. and at 5% carbon dioxide.

Determination of the luciferase activity: Briefly, the transfected cells were washed twice with 500 μl of PBS (phosphate buffer) and then lysed with 250 μl of reagent (Promega cell culture lysis reagent, from the Luciferase Assay System kit).

An aliquot of 10 μl of supernatant of the lysate centrifuged (12,000×g) for 5 minutes at 4° C. was measured with the Wallac Victor2 luminometer (1420 Multilabel counter).

The luciferase activity was assayed by the emission of light in the presence of luciferin, of coenzyme A and of ATP for 10 seconds and expressed relative to 2000 treated cells. The luciferase activity was thus expressed as Relative Light Unit ("RLU") and normalized with the concentration of proteins in the sample obtained using a Pierce BCA kit (Rockford, Ill., USA).

The results, summarized in FIG. 2, show a high transfection activity for the three compounds tested (the acid-sensitive compounds A Syn and Trans and the control cationic lipid). No significant difference was observed between them. In the absence of serum, the level of transfection was high in all the cases ($10^5$ to $10^7$ RLU/µg of protein) and the transfecting power increases with the quantity of acid-sensitive compound or of control cationic lipid used. The presence of serum induces inhibition of transfection in all cases.

This example shows that the transfecting power of the acid-sensitive compound A in its Syn and Trans forms was preserved compared with its non-acid-sensitive analog (the control cationic lipid). More generally, the introduction of an acid-sensitive cyclic ortho-ester function into molecules of the cationic lipid type that were known to be useful in nonviral transfection did not destroy the capacity of these compounds to efficiently transfect DNA.

Example 9

Use of the Acid-Sensitive Compounds C and D as Nonionic Surfactants for the Colloidal Stabilization of DNA/Cationic Lipid Transfecting Complexes This example illustrates the fact that the acid-sensitive pegoylated lipids of the type defined under (d) in the present application was used as nonionic surfactants that play a colloidal stabilizing role with respect to the DNA/cationic lipid transfecting particles.

In the present example, the cationic lipid used was that already used in examples 7 and 8 and described in the publication WO 97/18185 under the formula: $H_2N-(CH_2)_3-NH-(CH_2)_4-NH-(CH_2)_3-NH-CH_2-CO-Gly-N[(CH_2)_{17}-CH_3]_2$ (control cationic lipid).

Compounds C and D prepared in example 5 were used as acid-sensitive pegoylated lipids. As controls, there were used BRIJ 700 ((C18-$PEG_{5000}$, SIGMA) and the pegoylated lipid of formula:

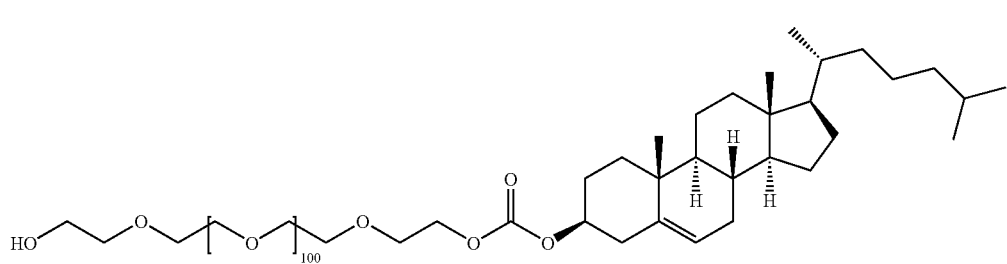

Analog D that were non-acid-sensitive analogs of compounds C and D, respectively, and that were known as nonionic surfactants (see for example the publication WO 98/34648). The two controls were used at 10 g/l in water.

1 ml samples of nucleolipid complexes (DNA/control cationic lipid) were prepared from DNA at 10 µg/ml in 75 mM of a sodium chloride solution, by mixing in equal volume the solution containing the control cationic lipid and one of the pegoylated lipids (compound C or compound D or Brij 700 or the analog D) with the DNA solution. All these samples had a control cationic lipid/DNA ratio of 1.5 (in nmol of lipid per µg of DNA) and contained increasing quantities of pegoylated lipid (expressed as polymer/DNA weight/weight ratio).

The measurement of the size of the particles obtained was made 30 minutes after the mixing and made it possible, for example, to study the influence of the quantity of acid-sensitive pegoylated lipid (compound C or D) or of the non-acid-sensitive pegoylated lipid (Brij 700 or analog D) on the stabilization of the control cationic lipid/DNA complexes. The measurement of the hydrodynamic diameter was made with a Coulter N4Plus apparatus using plastic cuvettes (four transparent sides) filled with 800 µl of the different solutions containing 0.01 mg of DNA/ml, the measurement being carried out at 90° C. in unimodal mode.

The results are presented in FIG. 3 which describes the variation in the size of the control cationic lipid/DNA particles as a function of the quantity of compound C or D or of Brij 700 or of analog D used.

It was observed that the acid-sensitive pegoylated lipids, as well as their stable controls, allowed the formation of small-sized (less than 100 nm) control cationic lipid/DNA particles when a minimal quantity was reached, whereas these same control cationic lipid/DNA particles spontaneously aggregated (size greater than 1 µm) in the absence of acid-sensitive or non-acid-sensitive pegoylated lipid or when the quantity of the latter was too low.

This example thus demonstrates that compounds C and D, and more generally acid-sensitive pegoylated lipids of the type defined under (d) in the general formula (I) of the present application, could be used as nonionic surfactants, and their colloidal stabilizing power was comparable to that of the stable nonionic surfactants (that was to say non-acid-sensitive such as Brij 700 for example) that were conventionally used for the colloidal stabilization of nucleolipid particles.

Example 10

Influence of the pH on the Colloidal Stabilization of DNA/Cationic Vector Complexes by Compounds C and D This example illustrates the fact that acid-sensitive pegoylated lipids of the type defined under (d) in the general formula (I) of the present application, and that were used as nonionic surfactants for stabilizing DNA/cationic lipid nucleolipid complexes, could be degraded at acidic pH and thus release said nucleolipid complexes.

The remarkable property that was used here was the absence of colloidal stabilization when a pegoylated lipid was replaced with a PEG without a lipid portion. Indeed, the formulation of the DNA in the presence of a cationic vector and of an acid-sensitive pegoylated lipid led, in a non-buffered medium, to small particles (see example 9 above). The same study with a PEG alone (that was to say not coupled to a lipid portion) does not, on the other hand, give any stabilization.

The acid-sensitive pegoylated lipid used in this example was the compound D prepared in example 5, as well as its non-acid-sensitive analog called "Analog D" in the preceding example and in the text that follows.

1 ml samples of nucleolipid complexes (DNA/control cationic lipid) were prepared from DNA at 10 µg/ml in 75 mM of a sodium chloride solution, by mixing in equal volume the solution containing the control cationic lipid and compound D or the non-acid-sensitive analog D with the DNA solution. All these samples had a control cationic lipid/DNA ratio of 1.5 (in nmol of lipid per µg of DNA). and contained increasing quantities of pegoylated lipid (expressed as polymer/DNA weight/weight ratio).

100 µl of acetic acid/sodium acetate buffer at pH 5 (0.1 mol/l) were added to these samples thermostated at 37° C. in a ventilated oven. The size of the particles was measured as a function of time.

The results obtained are represented in FIG. 4 which represents the size of the nucleolipid particles as a function of time, and also according to the acid-sensitive or non-acid-sensitive pegoylated lipid/DNA ratio (3 weight/weight ratios tested: 0.5 or 0.75 or 1).

In the case of analog D (non-acid-sensitive pegoylated lipid), the pH has no influence on the colloidal stability of the particles: the particles formed had a small size, of the order of 100 nm, regardless of the analog D/DNA ratio used. At time t=0, the same stability was observed with compound D, regardless of the compound D/DNA ratio.

On the other hand, an increase in the size of the nucleolipid particles as a function of time was observed when compound D was used as nonionic surfactant at acidic pH (pH 5). The lower the compound D/DNA ratio, the more rapid this increase in size of the nucleolipid particles. Thus, after 4 hours, the particles had completely formed into aggregates in the case of a low ratio (of 0.5) and not at all or only slightly when a large excess of compound D was used (ratio of 1).

It was thus possible to deduce therefrom that compound D was sensitive to the pH value. Indeed, the increase in the size of the nucleolipid particles as a function of time reflects the degradation of the acid-sensitive pegoylated lipid (compound D) when an acidic medium was used (there was in fact "ungrafting" of the lipid portion at the level of the acid-sensitive portion of the compound).

In addition, by increasing the acid-sensitive pegoylated lipid/DNA ratio, the time necessary for the aggregation was also increased, that tends to show that the more the acid-sensitive pegoylated lipid was used, the more of it there was to be degraded before crossing the threshold beyond that aggregation of the nucleolipid particles occurs. It was thus possible, by adjusting the quantity of acid-sensitive colloidal stabilizer, to program the time necessary for the release of the active ingredient at a given pH.

Example 11

Study of the Stability of the Acid-Sensitive Compounds as a Function of the pH

This example illustrates the fact that the acid-sensitive compounds according to the present invention had an acid-sensitivity that was modulable according to the nature of the ortho-ester ring present (5- or 6-membered ring).

To this effect, the variation of the size of nucleolipid complexes (identical to those used in examples 9 and 10) was measured as a function of the pH and time, for various acid-sensitive pegoylated lipids, that made it possible to cover different ranges of sensitivity. These studies were carried out at fixed control cationic lipid/DNA and acid-sensitive pegoylated lipid/DNA ratios.

1 ml samples of DNA/control cationic lipid/acid-sensitive pegoylated lipid complex were prepared such that:
the control cationic lipid/DNA ratio was 1.5 nmol/µg,
the acid-sensitive pegoylated lipid/DNA ratio was 0.5 or 1, and
the DNA concentration was 20 µg/ml in 75 mM of a sodium chloride solution.

After 30 minutes, 500 µl of a buffer solution at 0.05 mol/l and 500 µl of a sodium chloride solution at 150 mM were added to these samples thermostated at 37° C. in a ventilated oven. An acidic pH was thus established and the size of the particles was measured as a function of time.

The final concentration of the samples was 10 µg of DNA/ml in 75 mM of a sodium chloride solution. The buffers used were citric acid/sodium citrate buffers at pH 4, pH 5 and pH 6 and a Hepes/sodium hydroxide buffer at pH 7.4.

The results obtained were represented in FIG. 5 that represents the variation in the size of the nucleolipid particles as a function of the pH and of time for the acid-sensitive compounds C and E prepared in the preceding examples, and that differ only in the nature of the ortho-ester ring used (5- or 6-membered ring).

For these two compounds, an increase was observed in the size of the nucleolipid particles as a function of time when the pH was acidic, that reflects their degradation. On the other hand, an increase in the size of the nucleolipid particles as a function of time was not observed when the pH was 7.4. In addition, the lower the pH, the more rapid the aggregation of the nucleolipid particles.

Finally, a large difference in kinetics was observed between the two compounds C and E tested: at pH 6, the aggregation of the nucleolipid particles started about 1 hour after the acidification in the case of the use of compound E, whereas the use of the compound C allowed stabilization for at least 4 hours.

These results demonstrate several remarkable properties of the acid-sensitive compounds C and E, and more generally of the acid-sensitive compounds of this type according to the present application:
they both exhibited high sensitivity at acidic pH values, and in all cases, it was observed that the lower the pH, the more rapid their destabilization,
they were both relatively stable at physiological pH (pH of 7.4), and
their kinetics of degradation was very different depending on the ortho-ester group used (5- or 6-membered ring).

Example 12

The Dose Response of Two pH Labile PEG$_{5000}$-Lipids on Gene Transfer Activity of Cationic Lipid/DOPE/DNA Complexes in Vivo This example illustrates the fact that the -acid-sensitive compounds according to the present invention were effective vehicles for gene-transfer in vivo.

Liposome Preparation
The cationic lipid of formula:

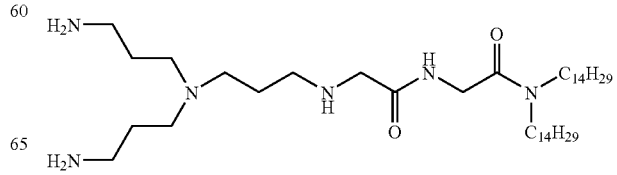

and DOPE (Avanti Polar Lipids (Birmingham, Ala.) were dissolved in chloroform and mixed in equimolar amounts. Then appropriate amounts of PEG-lipids were also dissolved in chloroform and added to this mixture. PEG-lipids added were compound C, compound D, or Analog D. Amounts of PEG-lipids used are given in mol % of total lipid. The organic solvent was evaporated under a stream of argon gas to form a thin film on the bottom of a glass tube. The film was vacuum-desiccated for at least one hour then allowed to hydrate in 20 mM HEPES pH7.4+5% Dextrose at 4° C. for two hours. The hydrated lipid suspension was heated to 50° C. for 30 minutes, then sonicated (Ultrasonic Cleaner, Laboratory Supplies, Hicksville, N.Y.) for 5 minutes to form a homogeneous suspension of liposomes of approximately 100 nm.

Plasmid DNA

Plasmid DNA contained the CAT reporter gene (in vivo experiments), under control of a CMV promoter. Purified plasmid DNA met the following quality criteria: Endotoxin levels <20 EU/mg; amount supercoiled DNA >90%; *E. coli* DNA contamination <5%; RNA contamination <5%; protein contamination <1%.

Lipid/DNA Complex Preparation

Equal volumes of liposome suspension (at the appropriate concentration) were added to the DNA stock solution while rapidly and thoroughly mixing by a few aspiration-injection cycles of a pipette. Typically, one μg DNA was complexed with 5 nmoles of cationic lipid. The complexes were approximately 100 to 240 nm in diameter as determined by dynamic light scattering with a Coulter N4+ particle sizer.

In Vivo Administration

Female Balb/C mice, approximately 6 weeks old, were used in all experiments. Each mouse was injected subcutaneously with 1×10$^6$ M109 cells in the right flank. When the tumors reached a size of about 300 mm$^3$ the mice received 200 μl lipid/DNA complex, containing 50 μg DNA, by tail vein injection. The tissues were harvested 24 hours after injection and stored at −70° C. until further use.

CAT Assay

The tissues were homogenized using a FastPrep Cell Disrupter FP120 (BIO 101/Savant). The samples were centrifuged at 1000 rpm at 4° C., for 5 minutes. The amount of CAT transgene expressed was determined using a standard CAT ELISA (Roche, Ind.).

Results

The dose response of two pH labile PEG$_{5000}$-lipids on gene transfer activity of the cationic lipid/DOPE/DNA complexes was investigated in vivo. The two compounds studied were C18-ortho-mPEG$_{5000}$ (compound C) and cholesterol-ortho-mPEG$_{5000}$ (compound D). C18-PEG$_{5000}$ (BRIJ700) and cholesterol-PEG-$_{5000}$ (Analog D) were used as respective negative controls. As expected the highest level of gene transfer with non-PEGylated formulations was observed in lungs. The level of gene transfer in M109 subcutaneous tumors was about 100-fold lower than in lungs. Gene transfer activity of both C18-ortho-mPEG$_{5000}$ (compound C) and the C18-PEG$_{5000}$ (BRIJ700) were similar to the complex without PEG at all doses in both lungs and tumor tissues. This strongly suggests that the single acyl chain C18-PEG lipids are lost from the particles due to their high water solubility, i.e. irrespective of their pH sensitive linker (FIG. 7).

Non-degradable cholesterol-PEG-$_{5000}$ inhibited gene transfer to both lungs and tumors in a dose-dependent-fashion. Increasing the amount of pH sensitive compound D also inhibited the gene transfer activity in lungs. As expected from the hypothesis that the acidic tumor environment would allow PEG to be released from particles after extravasation, the gene transfer activity of complexes bearing increasing amounts of pH sensitive PEG-cholesterol (compound D) appeared to be unaffected in the tumor. As a result, compound D increased the specific gene transfer activity of tumor/lung by 40 fold (FIG. 8).

What is claimed is:

1. A composition comprising at least one acid-sensitive compound, or a salt thereof, wherein the at least one acid-sensitive compound, or a salt thereof comprises (a) a cyclic ortho-ester and (b) at least one hydrophilic substituent or at least one hydrophobic substituent; wherein the at least one hydrophilic substituent is chosen from polyalkylene glycols, polyalkylene imine, monosaccharides, and polysaccharides; and wherein the at least one hydrophobic substituent is chosen from (i) steroid derivatives chosen from sterols, steroids, steroid hormones, cholesterol, cholestanol, 3-α-5-cyclo-5-α-cholestan-6-β-ol, cholic acid, cholesteryl formate, cholestanyl formate, 3α,5-cyclo-5α-cholestan-6β-yl formate, cholesterylamine, 6-(1,5-dimethylhexyl)-3a,5a-dimethylhexadecahydrocyclopenta[a]cyclopropa[2,3]cyclopenta[1,2-f]naphthalen-10-ylamine, cholestanylamine, and dexamethasone; and (ii) hydrophobic dendrimers; and the composition comprises at least one pharmaceutically acceptable vehicle.

2. The composition according to claim 1, comprising at least one acid-sensitive compound of formula (I):

or a salt thereof,
wherein:
g is an integer chosen from 0, 1, 2, 3 or 4,
G is a hydrogen atom, a straight or branched alkyl group comprising 1 to 6 carbon atoms optionally comprising at least one unsaturation, or an aryl group,
G$_1$ and G$_2$ is a pair of substituents chosen from one of the following substituent pairs:
(a) wherein one substituent is a hydrophilic substituent chosen from a linear or branched alkyl group comprising at least 3 carbon atoms, wherein at least one of the methylene groups is optionally replaced with an amino group that is optionally substituted with at least one methyl group, and wherein at least one terminal methyl group of said linear or branched alkyl groups are substituted with at least one primary amine, secondary amine, tertiary amine, quaternary amine, guanidine, or cyclic guanidine, and the other substituent is a hydrophobic substituent chosen from (i) steroid derivatives chosen from sterols, steroids, steroid hormones, cholesterol, cholestanol, 3-α-5-cyclo-5-α-cholestan-6-β-ol, cholic acid, cholesteryl formate, cholestanyl formate, 3α, 5-cyclo-5α-cholestan-β-yl formate, cholesterylamine, 6-(1,5-dimethylhexyl)-3a,5a-dimethylhexadecahydrocyclopenta[a]cyclopropa[2,3]cyclopenta[1,2-f]naphthalen-10-ylamine, cholestanylamine, and dexamethasone; and
(ii) hydrophobic dendrimers;

(b) or wherein one substituent is a hydrophilic polyalkylene glycol, a monosaccharide, or a polysaccharide, and the other substituent is a polyalkylene imine;

(c) or wherein one substituent is a polyalkylene glycol, polyalkylene imine, monosaccharide, or polysaccharide, and the other substituent is a single-chain alkyl, double-chain alkyl, steroid derivative, hydrophobic dendrimer, or a covalent conjugate between a single-chain alkyl, a double-chain alkyl, a steroid derivative, or a hydrophobic dendrimer and a polyalkylene glycol molecule comprising 1 to 20 monomeric units;

wherein the steroid derivatives is chosen from sterols, steroids, steroid hormones, cholesterol, cholestanol, 3-α-5-cyclo-5-α-cholestan-6-β-ol, cholic acid, cholesteryl formate, cholestanyl formate, 3α, 5-cyclo-5α-cholestan-6β-yl formate, cholesterylamine, 6-(1,5-dimethylhexyl)-3a,5a-dimethylhexadecahydrocyclopenta[a]cyclopropa[-2,3]cyclopenta[1,2-f]naphthalen-10-ylamine, cholestanylamine, and dexamethasone;

(d) or wherein one substituent is a polyalkylene glycol, a monosaccharide, or a polysaccharide, and the other substituent is a therapeutic molecule;

(e) or wherein one substituent is a hydrophilic therapeutic molecule, and the other substituent is a steroid derivative chosen from sterols, steroids, steroid hormones, cholesterol, cholestanol, 3-α-5-cyclo-5-α-cholestan-6-β-ol, cholic acid, cholesteryl formate, cholestanyl formate, 3α,5-cyclo-5α-cholestan-6β-yl formate, cholesterylamine, 6-(1,5-dimethylhexyl)-3a,5a-dimethylhexadecahydrocyclopenta[a]cyclopropa[-2,3]cyclopenta[1,2-f]naphthalen-10-ylamine, cholestanylamine, and dexamethasone, or a hydrophobic dendrimers.

3. The composition according to claim 2, wherein $G_1$ and $G_2$ of said acid-sensitive compound are defined as in said substituent pairs (a), (b), (c) or (d); and wherein said composition further comprises at least one biologically active substance.

4. The composition according to claim 3, wherein said biologically active substance is a nucleic acid, a peptide, an oligopeptide, a protein, an antigen, an antibody to said antigen, an enzyme, an inhibitor of said enzyme, a hormone, an antibiotic, an analgesic, a bronchodilator, an antimicrobial, an antihypertensive agent, a cardiovascular agent, an agent that acts on the central nervous system, an antihistamine, an antidepressant, a tranquilizer, an anticonvulsant, an anti-inflammatory substance, a stimulant, an antiemetic agent, a diuretic agent, an antispasmodic agent, an antiischemic agent, an agent limiting cell death, or an anticancer agent.

5. The composition according to claim 1, further comprising at least one adjuvant.

6. The compositions according to claim 5, wherein said adjuvant comprises at least one neutral lipid.

7. The composition according to claim 6, wherein said adjuvant comprises at least one neutral lipid chosen from natural zwitterionic lipids, synthetic zwitterionic lipids, and lipids lacking an ionic charge under physiological conditions.

8. The composition according to claim 7, wherein said adjuvant comprises at least one neutral lipid chosen from dioleoylphosphatidylethanolamine (DOPE), oleoyl-palmitoylphosphatidylethanolamine (POPE), distearoyl-phosphatidylethanolamine (DSPE), dipalmitoylphosphatidylethanolamine (DPPE), dimirystoylphosphatidylethanolamine (DMPE), DOPE N-methylated 1 to 3 times, POPE N-methylated 1 to 3 times, DSPE N-methylated 1 to 3 times, DPPE N-methylated 1 to 3 times, phosphatidylglycerols, diacylglycerols, glycosyldiacylglycerols, cerebrosides, sphingolipids, and asialogangliosides.

9. The composition according to claim 8, wherein said adjuvant comprises at least one cerebroside chosen from galactocerebrosides.

10. The composition according to claim 8, wherein said adjuvant comprises at least one sphingolipid chosen from sphingomyelins.

11. The composition according to claim 8, wherein said adjuvant comprises at least one asialogangliosides chosen from asialoGM1 and asialoGM2.

12. The composition according to claim 1, further comprising a pharmaceutically acceptable vehicle for an injectable formulation.

13. The composition according to claim 1, further comprising a pharmaceutically acceptable vehicle for administration to skin or mucous membranes.

* * * * *

UNITED STATES PATENT AND TRADEMARK OFFICE
CERTIFICATE OF CORRECTION

PATENT NO. : 7,641,914 B2  Page 1 of 1
APPLICATION NO. : 11/054612
DATED : January 5, 2010
INVENTOR(S) : Michael Bessodes et al.

It is certified that error appears in the above-identified patent and that said Letters Patent is hereby corrected as shown below:

Claim 2, column 42, lines 62-63, "3α 5-cyclo-5α-cholestan-β-yl" should read --3α,5-cyclo-5α-cholestan-6β-yl--.

Claim 2, column 43, line 2, "monosaccharide,or" should read --monosaccharide, or--.

Claim 2, column 43, lines 15-16, "3α, 5-cyclo-5α-cholestan-6β-yl" should read --3α,5-cyclo-5α-cholestan-6β-yl--.

Claim 2, column 43, lines 16-19, "6-(1,5-dimethylhexyl)-3a,5a-dimethylhexadecahydrocyclopental[a]cyclopropa[-2,3]cyclopental[1,2-f]naphthalen-10-ylamine," should read --6-(1,5-dimethylhexyl)-3a,5a-dimethylhexadecahydrocyclopental[a]cyclopropa[2,3]cyclopental[1,2-f]naphthalen-10-ylamine,--.

Claim 2, column 43, lines 29-31, "6-(1,5-dimethylhexyl)-3a,5a-dimethylhexadecahydrocyclopental [a]cyclopropa[-2,3]cyclopental[1,2-f]naphthalen-10-ylamine," should read --6-(1,5-dimethylhexyl)-3a,5a-dimethylhexadecahydrocyclopental [a]cyclopropa[2,3]cyclopental[1,2-f]naphthalen-10-ylamine,--.

Claim 2, column 43, line 32, "or a hydrophobic" should read --or hydrophobic--.

Claim 6, column 44, line 9, "compositions" should read --composition--.

Signed and Sealed this

Twenty-third Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,641,914 B2  Page 1 of 1
APPLICATION NO. : 11/054612
DATED : January 5, 2010
INVENTOR(S) : Bessodes et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1334 days.

Signed and Sealed this

Sixteenth Day of November, 2010

David J. Kappos
*Director of the United States Patent and Trademark Office*